(12) United States Patent
Dennis et al.

(10) Patent No.: US 10,087,407 B2
(45) Date of Patent: Oct. 2, 2018

(54) METHODS, DEVICES AND SYSTEMS FOR VIBRATION INDUCED TISSUE ENGINEERING

(71) Applicant: THE UNIVERSITY OF NORTH CAROLINA AT CHAPEL HILL, Chapel Hill, NC (US)

(72) Inventors: Robert G. Dennis, Chapel Hill, NC (US); John A. van Aalst, Walton, KY (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 51 days.

(21) Appl. No.: 15/066,506

(22) Filed: Mar. 10, 2016

(65) Prior Publication Data

US 2016/0230135 A1    Aug. 11, 2016

Related U.S. Application Data

(63) Continuation of application No. PCT/US2014/055219, filed on Sep. 11, 2014.
(Continued)

(51) Int. Cl.
*G01N 1/00* (2006.01)
*C12M 3/00* (2006.01)
(Continued)

(52) U.S. Cl.
CPC .............. *C12M 21/08* (2013.01); *A61F 2/02* (2013.01); *A61L 27/3691* (2013.01); *A61L 27/3817* (2013.01); *A61L 27/3821* (2013.01); *A61L 27/3895* (2013.01); *C12M 25/14* (2013.01); *C12M 35/02* (2013.01); *C12M 35/04* (2013.01); *C12M 41/46* (2013.01); *C12M 41/48* (2013.01); *C12N 5/0654* (2013.01); *C12N 5/0655* (2013.01); *C12N 5/0665* (2013.01); *A61L 2430/02* (2013.01); *A61L 2430/06* (2013.01);
(Continued)

(58) Field of Classification Search
CPC ........................................................ G01N 1/00
See application file for complete search history.

(56) References Cited

U.S. PATENT DOCUMENTS

2004/0158289 A1* 8/2004 Girouard ................ A61N 1/362
607/3

FOREIGN PATENT DOCUMENTS

WO    WO 2005-045008    5/2005

OTHER PUBLICATIONS

International Search Report and Written Opinion for PCT/US2014/055219 dated Dec. 29, 2014.
(Continued)

*Primary Examiner* — Jyoti Nagpaul
(74) *Attorney, Agent, or Firm* — Jenkins, Wilson, Taylor & Hunt, P.A.

(57) ABSTRACT

Methods, devices and systems are disclosed for vibration induced tissue engineering. Apparatuses, devices, systems and methods are provided for engineering a tissue from stem cells using vibratory signals. A tissue engineering apparatus, device, or system can include a transmitter configured to transmit a signal to a receiver, a receiver configured to receive a signal from a transmitter, a holding structure configured to hold one or more mesenchymal stem cells (MSC), and a vibratory actuator in communication with the receiver and configured to generate a vibratory signal that is applied to the MSC.

15 Claims, 8 Drawing Sheets

Specification includes a Sequence Listing.

Related U.S. Application Data

(60) Provisional application No. 61/876,513, filed on Sep. 11, 2013.

(51) Int. Cl.
    C12N 5/0775    (2010.01)
    C12M 1/42      (2006.01)
    C12M 1/36      (2006.01)
    A61F 2/02      (2006.01)
    A61L 27/36     (2006.01)
    A61L 27/38     (2006.01)
    C12M 1/12      (2006.01)
    C12M 1/34      (2006.01)
    C12N 5/077     (2010.01)

(52) U.S. Cl.
    CPC .. C12N 2506/1369 (2013.01); C12N 2527/00 (2013.01)

(56) References Cited

OTHER PUBLICATIONS

Caplan, A. I., "Adult Mesenchymal Stem Cells for Tissue Engineering Versus Regenerative Medicine," pp. 341-347, Jun. 4, 2007.
Cashion, Avery T. et al., "Programmable Mechanobioreactor for Exploration of the Effects of Periodic Vibratory Stimulus on Mesenchymal Stem Cell Differentiation," BioResearch Open Access, vol. 3, No. 1, pp. 19-28, Feb. 2014.
Delaine-Smith, Robin M. et al., "Mesenchymal stem cell responses to mechanical stimuli," Muscles, Ligaments and Tendons Journal, 2012, vol. 2, No. 3, pp. 169-180.
Elder, Steven H. et al., "Chondrocyte differentiation is modulated by frequency and duration of cyclic compressive loading," Annals of Biomedical Engineering, 2001, vol. 29, No. 6, pp. 476-482.
Pre, D. et al., "High-Frequency Vibration Treatment of Human Bone Marrow Stromal Cells Increases Differentiation toward Bone Tissue," Bone Marrow Research, Mar. 25, 2013, vol. 2013, Article ID 803450.
Tirkkonen, Laura et al., "The effects of vibration loading on adipose stem cellnumber, viability and diffemetiation towards bone-forming cells," Journal of Royal Society Interface, 2011, vol. 8, No. 65, pp. 1736-1747.
Kaya, M. et al., "Acoustic radiation force for vascular cell therapy: in vitro validation.," Ultrasound in medicine & biology, vol. 38, No. 11, pp. 1989-1997, Nov. 2012.
A. C. Guyton and J. Edward, Textbook of Medical Physiology, 11th ed. Elsevier Inc., 2006, pp. 27-42.
Alikhani, M., Khoo, E., Alyami, B., Raptis, M., Salgueiro, J.M., Oliveira, S.M., Boskey, A., and Teixeira, C.C., "Osteogenic Effect of High-frequency Acceleration on Alveolar Bone," Journal of dental research, vol. 91, No. 3, pp. 413-419, Apr. 2012.
Angele, P., Yoo, J.U., Smith, C., Mansour, J., Jepsen, K.J., Nerlich, M., and Johnstone, B., "Cyclic hydrostatic pressure enhances the chondrogenic phenotype of human mesenchymal progenitor cells differentiated in vitro," Journal of orthopaedic research : official publication of the Orthopaedic Research Society, vol. 21, No. 3, pp. 451-457, May 2003.
Bashardoust Tajali, S., Houghton, P., MacDermid, J.C., and Grewal, R., "Effects of low-intensity pulsed ultrasound therapy on fracture healing: a systematic review and meta-analysis," American journal of physical medicine & rehabilitation / Association of Academic Physiatrists, vol. 91, No. 4, pp. 349-367, Apr. 2012.
Bian, L., Zhai, D.Y., Zhang, E.C., Mauck, R.L., and Burdick, J.A., "Dynamic Compressive Loading Enhances Cartilage Matrix Synthesis and Distribution and Suppresses Hypertrophy in hMSC-Laden Hyaluronic Acid Hydrogels," vol. 18, 2012.
Brown, T.D., "Techniques for mechanical stimulation of cells in vitro: a review," Journal of biomechanics, vol. 33, No. 1, pp. 3-14, Jan. 2000.

Caballero, M., et al., "Osteoinduction in umbilical cord- and palate periosteum-derived mesenchymal stem cells," Annals of plastic surgery, vol. 64, No. 5, pp. 605-609, May 2010.
Cheung, W.H., et al., "Applications of exogenous mesenchymal stem cells and low intensity pulsed ultrasound enhance fracture healing in rat model," Ultrasound in medicine & biology, vol. 39, No. 1, pp. 117-125, Jan. 2013.
Cheung, W.H., et al., "Low intensity pulsed ultrasound enhances fracture healing in both ovariectomy-induced osteoporotic and age-matched normal bones," Journal of orthopaedic research: official publication of the Orthopaedic Research Society, vol. 30, No. 1, pp. 129-136, Jan. 2012.
Cheung, W.H., et al., "Stimulated angiogenesis for fracture healing augmented by low-magnitude, high-frequency vibration in a rat model-evaluation of pulsed-wave doppler, 3-D power Doppler ultrasonography and micro-CT microangiography," Ultrasound in medicine & biology, vol. 38, No. 12, pp. 2120-2129, Dec. 2012.
Chow, D.H., et al., "Low-magnitude high-frequency vibration (LMHFV) enhances bone remodeling in osteoporotic rat femoral fracture healing," Journal of orthopaedic research : official publication of the Orthopaedic Research Society, vol. 29, No. 5, pp. 746-752, May 2011.
Chung, S.L., et al., "Fracture healing enhancement with low intensity pulsed ultrasound at a critical application angle," Ultrasound in medicine & biology, vol. 37, No. 7, pp. 1120-1133, Jul. 2011.
Dahl, J.P., et al., "Analysis of human auricular cartilage to guide tissue-engineered nanofiber-based chondrogenesis: implications for microtia reconstruction," Otolaryngology—head and neck surgery: official journal of American Academy of Otolaryngology—Head and Neck Surgery, vol. 145, No. 6, pp. 915-923, Dec. 2011.
Dennis, R.G., et al., "Measurement of Pulse Propagation in single permabilized muscle fibers by optical diffraction," University of Michigan, Ann Arbor, MI, 1996.
Gaston, J., et al., "The response of vocal fold fibroblasts and mesenchymal stromal cells to vibration," PloS one, vol. 7, No. 2, p. e30965, Jan. 2012.
Griffin, XL, et al., "Ultrasound and shockwave therapy for acute fractures in adults ( Review )," No. 2, 2012.
Haugh, M.G., et al., "Temporal and spatial changes in cartilage-matrix-specific gene expression in mesenchymal stem cells in response to dynamic compression," Tissue engineering. Part A, vol. 17, No. 23-24, pp. 3085-3093, Dec. 2011.
Hilfiker, A., Kasper, C., Hass, R., Haverich, A., "Mesenchymal stem cells and progenitor cells in connective tissue engineering and regenerative medicine: is there a future for transplantation?" Langenbeck's archives of surgery / Deutsche Gesellschaft für Chirugie, vol. 396, No. 4, pp. 489-497, Apr. 2011.
Huang, C.C., et al., "Effects of Cyclic Compressive Loading on Chondrogenesis of Rabbit Bone-Marrow Derived Mesenchymal Stem Cells," Stem . . . , pp. 313-323, 2004.
Huang, C. H., Chen, M. H., Young, T. H., Jeng, J. H., and Chen, Y. H., "Interactive Effects of Mechanical Stretching and Extracellular Matrix Proteins on Initiating Osteogenic Differentiation of Human Mesenchymal Stem Cells," Journal of Cellular Biochemistry, vol. 108, No. 6, pp. 1263-1273, Dec. 2009.
Ingber, D.E., "Tensegrity : The Architectural Basis of Cellular Mechanotransduction," Annual review of physiology, vol. 59, pp. 575-599, 1997.
Kamotani, Y., et al., "Individually programmable cell stretching microwell arrays actuated by a Braille display," Biomaterials, vol. 29, No. 17, pp. 2646-2655, Jun. 2008.
Kearney, E.M., et al., "Tensile strain as a regulator of mesenchymal stem cell osteogenesis," Annals of biomedical engineering, vol. 38, No. 5, pp. 1767-1779, May 2010.
Kim, I.S., et al., "Human mesenchymal stromal cells are mechanosensitive to vibration stimuli," Journal of dental research, vol. 91, No. 12, pp. 1135-1140, Dec. 2012.
Ku, C.-H. et al., "Collagen synthesis by mesenchymal stem cells and aortic valve interstitial cells in response to mechanical stretch," Cardiovascular research, vol. 71, No. 3, pp. 548-556, Aug. 2006.
Lai, C.-H., et al., "Effects of low-intensity pulsed ultrasound, dexamethasone/TGF-beta/ and/or BMP-2 on the transcriptional expression of genes in human mesenchymal stem cells: chondrogenic

(56) References Cited

OTHER PUBLICATIONS vs. osteogenic differentiation," Ultrasound in medicine & biology, vol. 36, No. 6, pp. 1022-1033, Jun. 2010.

MacQueen, L., et al., "Mesenchymal stem cell mechanobiology and emerging experimental platforms," Journal of the Royal Society, Interface / the Royal Society, vol. 10, No. 84, p. 20130179, Jul. 2013.

MacQueen, L., et al., "Miniaturized platform with on-chip strain sensors for compression testing of arrayed materials," Lab on a chip, vol. 12, No. 20, pp. 4178-4184, Oct. 2012.

Moraes, C., et al., "Microfabricated arrays for high-throughput screening of cellular response to cyclic substrate deformation," Lab on a chip, vol. 10, No. 2, pp. 227-234, Jan. 2010.

Moraes, C., et al., "A microfabricated platform for high-throughput unconfined compression of micropatterned biomaterial arrays," Biomaterials, vol. 31, No. 3, pp. 577-584, Jan. 2010.

Potter, E., Noailly, J., and Ito, K., "Directing bone marrow-derived stromal cell function with mechanics," Journal of Biomechanics, vol. 43, No. 5, pp. 807-817, Mar. 2010.

Puetzer, J., et al., "The effects of cyclic hydrostatic pressure on chondrogenesis and viability of human adipose- and bone marrow-derived mesenchymal stem cells in three-dimensional agarose constructs," Tissue engineering. Part A, vol. 19, pp. 299-306, 2013.

Richardson, S. M., Hoyland, J. A., Mobasheri, R., Csaki, C., Shakibaei, M., and Mobasheri, A., "Mesenchymal Stem Cells in Regenerative Medicine: Opportunities and Challenges for Articular Cartilage and Intervertebral Disc Tissue Engineering," Journal of Cellular Physiology, vol. 222, No. 1, pp. 23-32, Jan. 2010.

Rutten, S., et al., "Low-intensity pulsed ultrasound increases bone volume, osteoid thickness and mineral apposition rate in the area of fracture healing in patients with a delayed union of the osteotomized fibula," Bone, vol. 43, No. 2, pp. 348-354, Aug. 2008.

Shi, H., et al., "Low-magnitude high-frequency vibration treatment augments fracture healing in ovariectomy-induced osteoporotic bone," Bone, vol. 46, No. 5, pp. 1299-1305, May 2010.

Tsuang, Y.H., et al., "Effect of dynamic compression on in vitro chondrocyte metabolism," The International journal of artificial organs, vol. 31, No. 5, pp. 439-449, May 2008.

Uzer, G., et al., "Vibration induced osteogenic commitment of mesenchymal stem cells is enhanced by cytoskeletal remodeling but not fluid shear," Journal of biomechanics, pp. 1-7, Jul. 2013.

Vogel, V., et al., "Cell fate regulation by coupling mechanical cycles to biochemical signaling pathways," Current. opinion in cell biology, vol. 21, No. 1, pp. 38-46, Feb. 2009.

Wolchok, J.C., et al., "The effect of bioreactor induced vibrational stimulation on extracellular matrix production from human derived fibroblasts," Biomaterials, vol. 30, No. 3, pp. 327-335, Jan. 2009.

Wu, S.H., et al., "Low-magnitude high-frequency vibration inhibits RANKL-induced osteoclast differentiation of RAW264.7 cells," International journal of medical sciences, vol. 9, No. 9, pp. 801-807, Jan. 2012.

Zhang, C., et al., "Effects of mechanical vibration on proliferation and osteogenic differentiation of human periodontal ligament stem cells," Archives of oral biology, vol. 57, No. 10, pp. 1395-1407, Oct. 2012.

\* cited by examiner

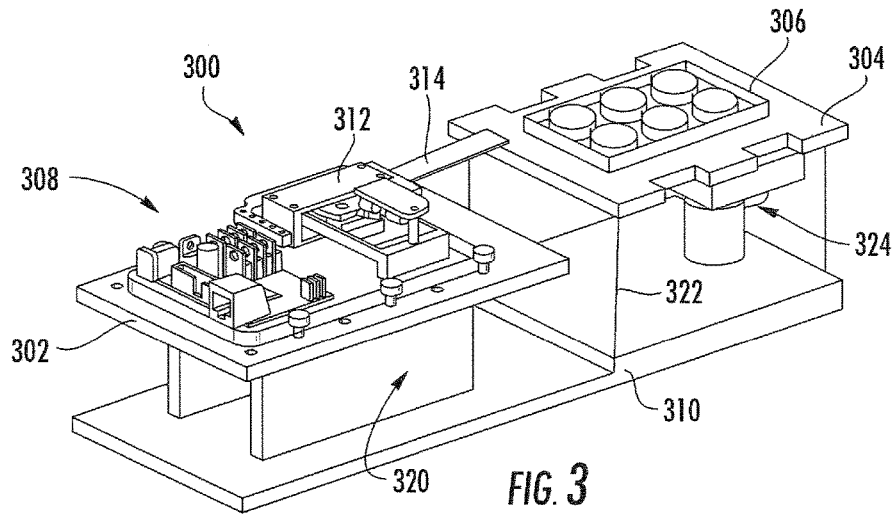
FIG. 3
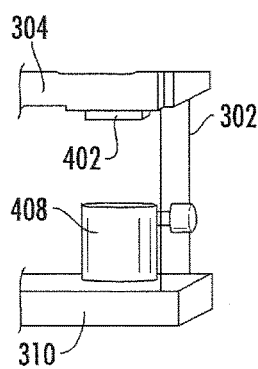
FIG. 4A
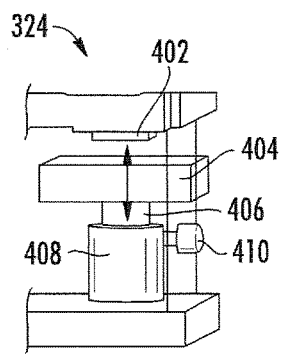
FIG. 4B
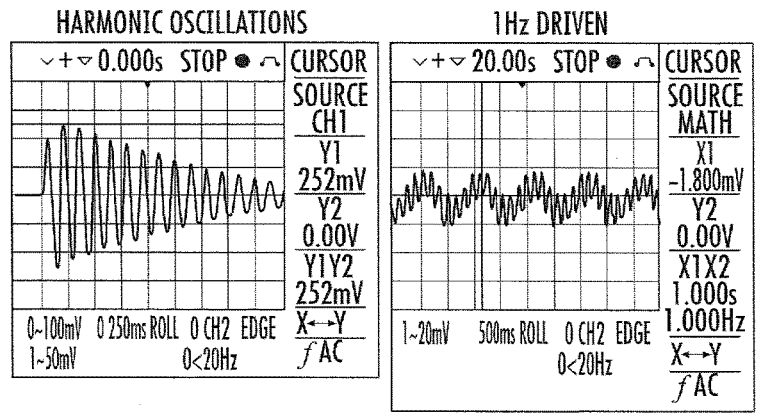
FIG. 4C
FIG. 4D
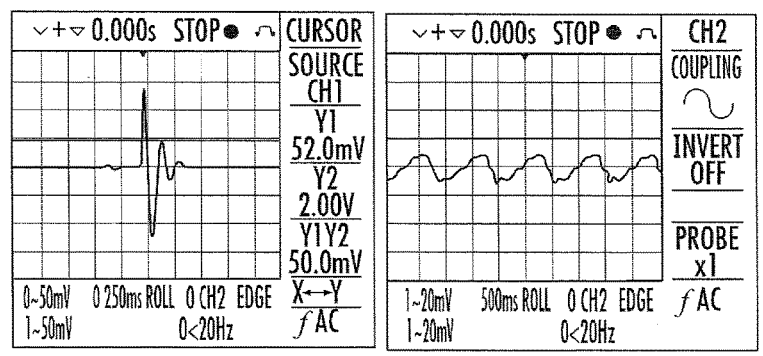
FIG. 4E
FIG. 4F

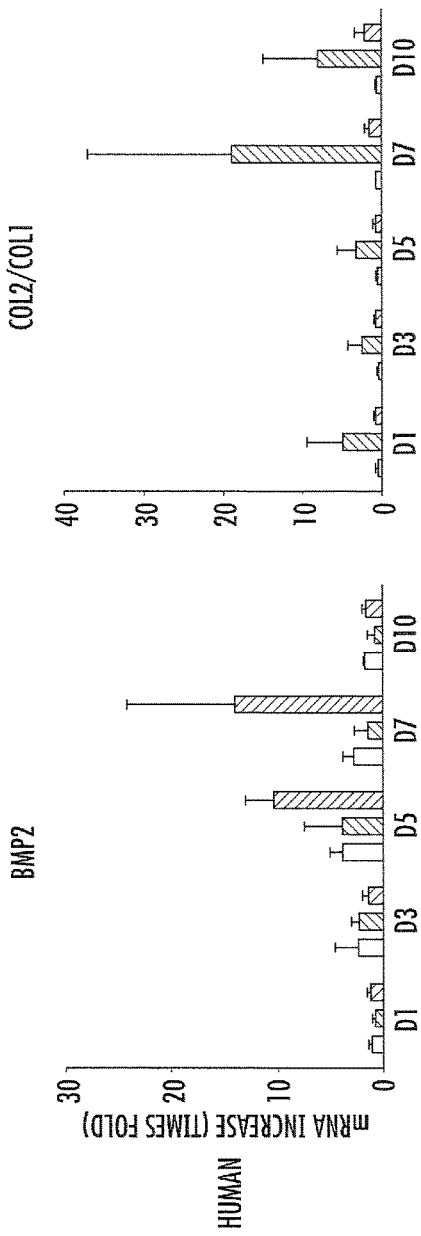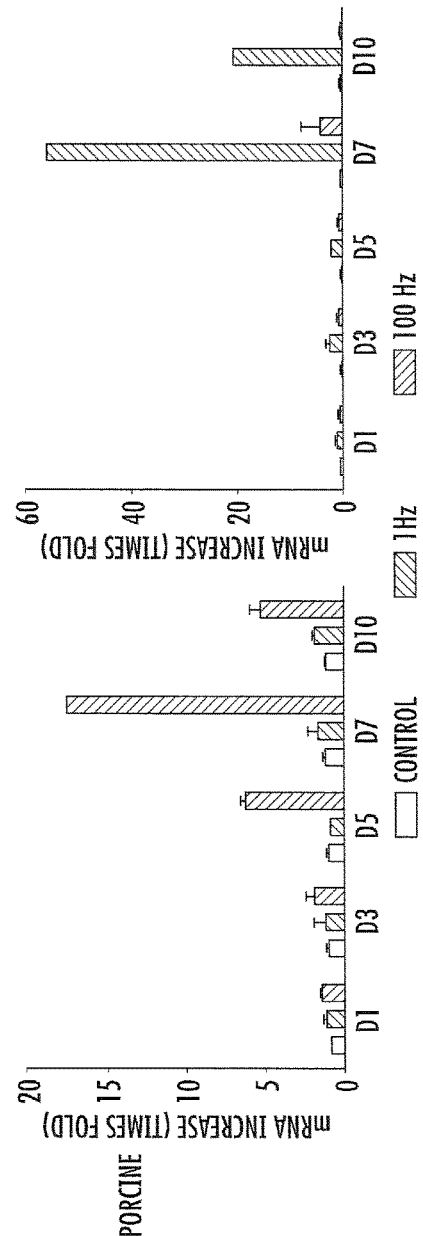
FIG. 6A  FIG. 6B  FIG. 6C  FIG. 6D

SEQUENCE LISTING

```
<160> NUMBER OF SEQ ID NOS: 24

<210> SEQ ID NO 1
<211> LENGTH: 19
<212> TYPE: DNA
<213> ORGANISM: Artificial Sequence
<220> FEATURE:
<223> OTHER INFORMATION: Artificially synthesized oligonucleotide

<400> SEQUENCE: 1
ccagaccacc ggttggaga                                                  19

<210> SEQ ID NO 2
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 2
ttccaaagat tcttcatggt gg                                              22

<210> SEQ ID NO 3
<211> LENGTH: 23
<212> TYPE: DNA
<213> ORGANISM: Artificial Sequence
<220> FEATURE:
<223> OTHER INFORMATION: Artificially synthesized oligonucleotide
<220> FEATURE:
<221> NAME/KEY: misc_feature
<222> LOCATION: (1)..(23)
<223> OTHER INFORMATION: The probe can be labeled at the 5' position with a fluorescent
      label and/or at the 3' position with a quencher

<400> SEQUENCE: 3
agccagccga gccaacactg tgc                                             23

<210> SEQ ID NO 4
<211> LENGTH: 20
<212> TYPE: DNA
<213> ORGANISM: Artificial Sequence
<220> FEATURE:
<223> OTHER INFORMATION: Artificially Synthesized Oligonucleotide

<400> SEQUENCE: 4
aacagccgct tcacctacag                                                 20

<210> SEQ ID NO 5
<211> LENGTH: 20
<212> TYPE: DNA
<213> ORGANISM: Artificial Sequence
<220> FEATURE:
<223> OTHER INFORMATION: Artificially Synthesized Oligonucleotide

<400> SEQUENCE: 5
tcaatcactg tctttgccca                                                 20

<210> SEQ ID NO 6
```

```
<211> LENGTH: 24
<212> TYPE: DNA
<213> ORGANISM: Artificial Sequence
<220> FEATURE:
<223> OTHER INFORMATION: Artificially Synthesized Oligonucleotide
<220> FEATURE:
<221> NAME/KEY: misc_feature
<222> LOCATION: (1)..(24)
<223> OTHER INFORMATION: The probe can be labeled at the 5' position with a fluorescent
      label and/or at the 3' position with a quencher

<400> SEQUENCE: 6
tcgatggctg cacgagtcac accg                                              24

<210> SEQ ID NO 7
<211> LENGTH: 21
<212> TYPE: DNA
<213> ORGANISM: Artificial Sequence
<220> FEATURE:
<223> OTHER INFORMATION: Artificially Synthesized Oligonucleotide

<400> SEQUENCE: 7
caatagcagg ttcacgtaca c                                                 21

<210> SEQ ID NO 8
<211> LENGTH: 20
<212> TYPE: DNA
<213> ORGANISM: Artificial Sequence
<220> FEATURE:
<223> OTHER INFORMATION: Artificially Synthesized Oligonucleotide

<400> SEQUENCE: 8
tcgataacag tcttgcccca                                                   20

<210> SEQ ID NO 9
<211> LENGTH: 24
<212> TYPE: DNA
<213> ORGANISM: Artificial Sequence
<220> FEATURE:
<223> OTHER INFORMATION: Artificially Synthesized Oligonucleotide
<220> FEATURE:
<221> NAME/KEY: misc_feature
<222> LOCATION: (1)..(24)
<223> OTHER INFORMATION: The probe can be labeled at the 5' position
      with a fluorescent label and/or at the 3' position with a
      quencher

<400> SEQUENCE: 9
aggatggctg cacgaaacat accg                                              24

<210> SEQ ID NO 10
<211> LENGTH: 20
<212> TYPE: DNA
<213> ORGANISM: Artificial Sequence
<220> FEATURE:
<223> OTHER INFORMATION: Artificially Synthesized Oligonucleotide

<400> SEQUENCE: 10
agaaacggct accacatcca                                                   20

<210> SEQ ID NO 11
<211> LENGTH: 21
<212> TYPE: DNA
<213> ORGANISM: Artificial Sequence
<220> FEATURE:
<223> OTHER INFORMATION: Artificially Synthesized Oligonucleotide

<400> SEQUENCE: 11
```
ctcgaaagag tcctgtattg t         21

<210> SEQ ID NO 12
<211> LENGTH: 22
<212> TYPE: DNA
<213> ORGANISM: Artificial Sequence
<220> FEATURE:
<223> OTHER INFORMATION: Artificially Synthesized Oligonucleotide
<220> FEATURE:
<221> NAME/KEY: misc_feature
<222> LOCATION: (1)..(22)
<223> OTHER INFORMATION: The probe can be labeled at the 5' position
      with a fluorescent label and/or at the 3' position with a quencher

<400> SEQUENCE: 12
aggcagcagg cgcgcaaatt ac        22

<210> SEQ ID NO 13
<211> LENGTH: 18
<212> TYPE: DNA
<213> ORGANISM: Artificial Sequence
<220> FEATURE:
<223> OTHER INFORMATION: Artificially Synthesized Oligonucleotide

<400> SEQUENCE: 13
ggctggagag ggcagcca             18

<210> SEQ ID NO 14
<211> LENGTH: 21
<212> TYPE: DNA
<213> ORGANISM: Artificial Sequence
<220> FEATURE:
<223> OTHER INFORMATION: Artificially Synthesized Oligonucleotide

<400> SEQUENCE: 14
ctcatttctg gcagttcttc c         21

<210> SEQ ID NO 15
<211> LENGTH: 25
<212> TYPE: DNA
<213> ORGANISM: Artificial Sequence
<220> FEATURE:
<223> OTHER INFORMATION: Artificially Synthesized Oligonucleotide
<220> FEATURE:
<221> NAME/KEY: misc_feature
<222> LOCATION: (1)..(25)
<223> OTHER INFORMATION: The probe can be labeled at the 5' position
      with a fluorescent label and/or at the 3' position with a quencher

<400> SEQUENCE: 15
tggccaacac cgtgcgcagc ttcca     25

<210> SEQ ID NO 16
<211> LENGTH: 20
<212> TYPE: DNA
<213> ORGANISM: Artificial Sequence
<220> FEATURE:
<223> OTHER INFORMATION: Artificially Synthesized Oligonucleotide

<400> SEQUENCE: 16
gccaagaaga agacatccca           20

<210> SEQ ID NO 17
<211> LENGTH: 20
<212> TYPE: DNA
<213> ORGANISM: Artificial Sequence
<220> FEATURE:
<223> OTHER INFORMATION: Artificially Synthesized Oligonucleotide

<400> SEQUENCE: 17
tttccacacg tctcggtcat                                               20

<210> SEQ ID NO 18
<211> LENGTH: 25
<212> TYPE: DNA
<213> ORGANISM: Artificial Sequence
<220> FEATURE:
<223> OTHER INFORMATION: Artificially Synthesized Oligonucleotide
<220> FEATURE:
<221> NAME/KEY: misc_feature
<222> LOCATION: (1)..(25)
<223> OTHER INFORMATION: The probe can be labeled at the 5' position
      with a fluorescent label and/or at the 3' position with a quencher

<400> SEQUENCE: 18
agtcacctgc gtacagaacg gcctc                                         25

<210> SEQ ID NO 19
<211> LENGTH: 20
<212> TYPE: DNA
<213> ORGANISM: Artificial Sequence
<220> FEATURE:
<223> OTHER INFORMATION: Artificially Synthesized Oligonucleotide

<400> SEQUENCE: 19
tgtcacggcc aggatgtcca                                               20

<210> SEQ ID NO 20
<211> LENGTH: 21
<212> TYPE: DNA
<213> ORGANISM: Artificial Sequence
<220> FEATURE:
<223> OTHER INFORMATION: Artificially Synthesized Oligonucleotide

<400> SEQUENCE: 20
ggcttccaca catccttatc a                                             21

<210> SEQ ID NO 21
<211> LENGTH: 24
<212> TYPE: DNA
<213> ORGANISM: Artificial Sequence
<220> FEATURE:
<223> OTHER INFORMATION: Artificially Synthesized Oligonucleotide
<220> FEATURE:
<221> NAME/KEY: misc_feature
<222> LOCATION: (1)..(24)
<223> OTHER INFORMATION: The probe can be labeled at the 5' position
      with a fluorescent label and/or at the 3' position with a quencher

<400> SEQUENCE: 21
acctctgccc atcctgcacg cagc                                          24

<210> SEQ ID NO 22
<211> LENGTH: 20
<212> TYPE: DNA
<213> ORGANISM: Artificial Sequence
<220> FEATURE:
<223> OTHER INFORMATION: Artificially Synthesized Oligonucleotide

<400> SEQUENCE: 22
agaaacggct accacatcca                                               20

<210> SEQ ID NO 23
<211> LENGTH: 21
<212> TYPE: DNA

```
<213> ORGANISM: Artificial Sequence
<220> FEATURE:
<223> OTHER INFORMATION: Artificially Synthesized Oligonucleotide

<400> SEQUENCE: 23
ctcgaaagag tcctgtattg t                                              21

<210> SEQ ID NO 24
<211> LENGTH: 22
<212> TYPE: DNA
<213> ORGANISM: Artificial Sequence
<220> FEATURE:
<223> OTHER INFORMATION: Artificially Synthesized Oligonucleotide
<220> FEATURE:
<221> NAME/KEY: misc_feature
<222> LOCATION: (1)..(22)
<223> OTHER INFORMATION: The probe can be labeled at the 5' position
      with a fluorescent label and/or at the 3' position with a quencher

<400> SEQUENCE: 24
aggcagcagg cgcgcaaatt ac                                             22
```

METHODS, DEVICES AND SYSTEMS FOR VIBRATION INDUCED TISSUE ENGINEERING

CROSS-REFERENCE TO RELATED APPLICATIONS

This application is a continuation of and claims priority to PCT/US2014/055219 filed Sep. 11, 2014, which claims the benefit of and priority to U.S. Provisional Patent Application Ser. No. 61/876,513, filed Sep. 11, 2013, the entire disclosures of which are incorporated by reference herein.

GRANT STATEMENT

This invention was made with government support under grant no. DE023124 awarded by the National Institutes of Health. The government has certain rights in the invention.

TECHNICAL FIELD

The presently disclosed subject matter relates generally to methods, devices and systems for vibration induced tissue engineering. More particularly, the presently disclosed subject matter relates to apparatuses, devices, systems and/or methods for engineering a tissue from stem cells using vibratory signals.

BACKGROUND

Bone and cartilage defects, either individually or in combination, result from a wide variety of congenital anomalies, traumatic injury, and cancer extirpation. These defects are generally treated with autologous grafts that require a secondary surgical site, and can be associated with significant donor-site morbidity. The capacity of tissue engineering to provide solutions to these challenges is significant. The availability and versatility of mammalian mesenchymal stem cells (MSCs) for potential applications in tissue engineering and regenerative medicine has immense potential [1], [2], [3].

What are needed, then, are new strategies, methods, systems, devices and apparatuses for engineering a tissue from stem cells. The presently disclosed subject matter addresses this and other needs in the art.

SUMMARY

This summary lists embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this summary does not list or suggest all possible combinations of such features.

It is an object of the presently disclosed subject matter to provide methods, devices and systems for vibration induced tissue engineering. It is an object of the presently disclosed subject matter to provide apparatuses, devices, systems and/or methods for engineering a tissue from stem cells using vibratory signals.

An object of the presently disclosed subject matter having been stated above, other objects and advantages will become apparent to those of ordinary skill in the art after a study of the following description of the presently disclosed subject matter and non-limiting Examples.

BRIEF DESCRIPTION OF THE DRAWINGS

FIG. 3 is a perspective view of an in vitro bioreactor system;

FIGS. 4A-4F depict a damping mechanism of an in vitro bioreactor system and the effects thereof;

FIGS. 6A-6D are graphical depictions of the results of mRNA quantification in MSCs exposed to vibratory signals;

DETAILED DESCRIPTION

Provided herein are methods, devices and systems for vibration induced tissue engineering. In some embodiments, the presently disclosed subject matter relates to apparatuses, devices, systems and/or methods for engineering a tissue from stem cells using vibratory signals. The availability and versatility of mammalian mesenchymal stem cells (MSCs) provide the ability to engineer tissues for regenerative medicine applications.

The factors regulating cell fate of MSCs are widely varied and are not yet fully characterized or understood. Mature human cells generally produce a maximum of about 30% of the proteins the genome is capable of.[4] Cell differentiation is accepted as the selective repression of specific groups of genes, regardless of the mechanism of influence. The disclosed methods, devices and systems is based on the discovery that the combination of compressive, tensile and shear forces from an applied vibratory stimulus can generate bone formation at higher frequencies and a cartilage phenotype at lower frequencies.

Thus, in some embodiments, provided herein are methods, devices and systems for applying a vibratory signal or other mechanical influence to induce an osteogenic lineage, either in vitro or in vivo, which can be indicated by increases of BMP2 levels. Comparatively, in some embodiments, provided herein are methods, devices and systems for applying a vibratory signal or other mechanical influence to induce a chondrogenic lineage, either in vitro or in vivo, which can be indicated by increases in COL2/COL1. Osteogenesis and chondrogenesis can also be confirmed and/or measured by Alizarin Red and Alcian Blue staining, respectively.

In Vivo Tissue Engineering System and Implantable Bioreactor

Figure 1:
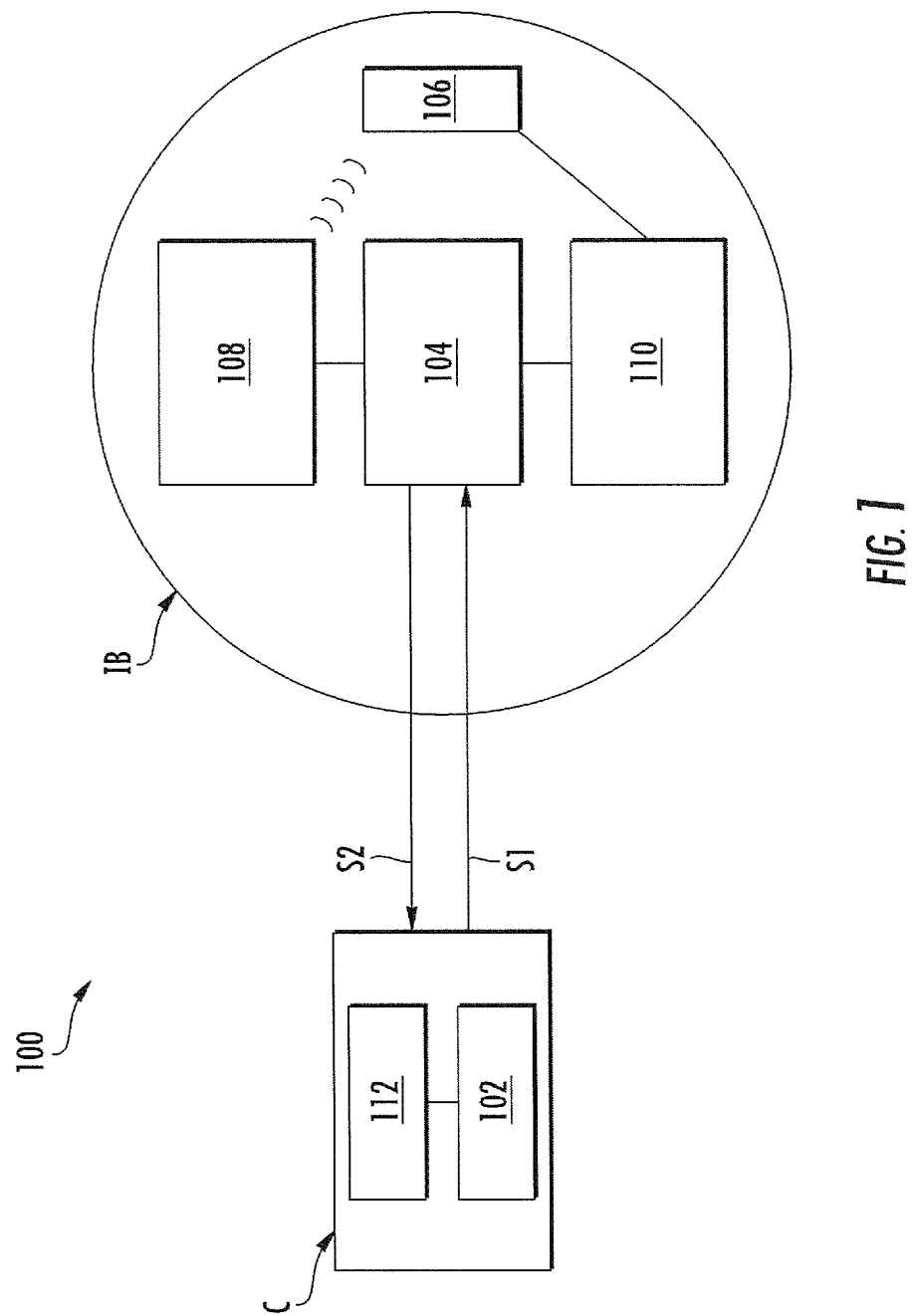
FIG. 1 is a schematic illustration of a tissue engineering bioreactor system.

In some embodiments, an apparatus, device and/or system for engineering a tissue is provided. A tissue engineering system is depicted in FIG. 1. Of note, the tissue engineering system as depicted in FIG. 1 is in schematic format for purposes of illustration but is not to scale. Tissue engineering system 100 can in some aspects comprise an external component, such as controller C, and an internal component, such as implantable bioreactor IB. Tissue engineering system 100 can in some aspects comprise a transmitter 102 configured to transmit a first signal S1 to a receiver 104. Receiver 104 can be configured to receive a first signal S1 from transmitter 102. Tissue engineering system 100 can further comprise a holding structure 106 configured to hold one or more stem cells, such as mesenchymal stem cells (MSC). Tissue engineering system 100 can in some aspects further comprise a vibratory actuator 108 in communication, e.g. electronic communication, with receiver 104 and configured to generate a vibratory signal VS. First signal S1 transmitted from transmitter 102 and received by the receiver 104 is communicated to vibratory actuator 108 to generate a vibratory signal VS, wherein vibratory signal VS is applied to holding structure 106 and thereby any stem cells, such as MSC, within holding structure 106. In some aspects, the receiver 104, holding structure 106 and vibratory actuator 108 are configured to be implantable in a subject, wherein transmitter 102 is configured to be external to the subject. In some aspects, transmitter 102 is ex vivo while the receiver 104 is in vivo. In some embodiments, tissue engineering system 100 can comprise a bioreactor configured to be implanted in a subject, such as depicted in further detail in FIG. 2.

In some embodiments, the transmitter, such as transmitter 102 in FIG. 1, can comprise any combination of a computer, processor, embedded system, microcontroller and/or computer readable medium, wherein the computer readable medium has stored thereon executable instructions that when executed by the processor of the computer cause the transmitter to transmit a desired signal, such as first signal S1. The signal transmitted by the transmitter and received by the receiver, e.g. first signal S1, can be a wireless signal.

In some aspects, vibratory signal VS generated by vibratory actuator 108 can have a frequency ranging from about 0.1 hertz to about 1000 hertz. In some aspects, vibratory signal VS generated by vibratory actuator 108 can have a frequency ranging from about 1 hertz to about 100 hertz.

In some embodiments, the stem cells, such as MSC, within holding structure 106 are in sufficient proximity to vibratory actuator 108 such that vibratory signal VS generated by vibratory actuator 108 is applied to the MSC, to a scaffold onto which MSCs are adhered, and/or to tissue into which MSCs have been delivered.

In some aspects, system 100 can further comprise a monitoring component 110 for monitoring the differentiation of the stem cells, or MSC, subsequent to application of vibratory signals VS. Monitoring component 110 can in some aspects be configured for non-damaging and/or non-destructive measurement or quantification of the differentiation of the MSC subsequent to application of vibratory signals VS within implantable bioreactor IB. Monitoring component 110 can use signals to exert feedback control over the course of tissue differentiation by routing a second signal S2 back to an external monitoring component 112, which in some aspects can be a component of controller C. In some embodiments, signals in a feedback control system can be used in which the real-time status of MSC development or phenotype may be conveyed to an external monitoring system, e.g. external monitoring component 112, using wireless signals. In some embodiments, the past time-course of MSC development or phenotype detected by monitoring component 110 can be stored within implantable bioreactor IB and may thereafter be conveyed to the external monitoring component 112 using wireless signals.

In some aspects, the frequency, duration, amplitude, waveform, and timing of vibratory signal VS can be adjusted depending on the differentiation of the MSC. In some embodiments, controller C, and particularly, transmitter 102, can send a return signal, by way of S1 for example, to receiver 104 in implantable bioreactor IB such that vibratory signal VS emitted by vibratory actuator 108 and applied to the stem cells within holding structure 106 is adjusted accordingly.

Figure 2:
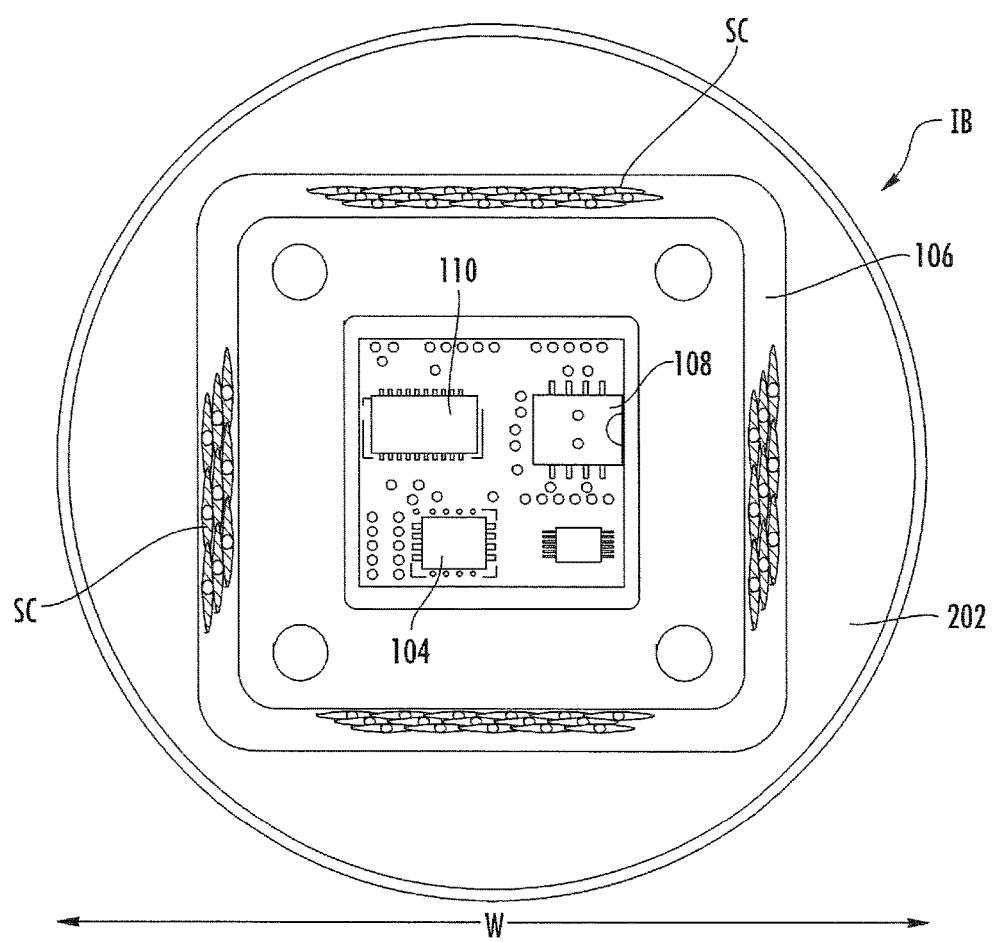
FIG. 2 is a plan view of an implantable bioreactor.

An exemplary implantable bioreactor IB is depicted in FIG. 2. Implantable bioreactor IB can comprise a receiver 104. Receiver 104 can be configured to receive a first signal S1 from transmitter (such as transmitter 102 depicted in FIG. 1). Implantable bioreactor IB can comprise can further comprise a holding structure 106 (or cell compartment) configured to hold one or more stem cells SC, such as mesenchymal stem cells (MSC). Implantable bioreactor IB can comprise can in some aspects further comprise a vibratory actuator 108 in communication, e.g. electronic communication, with receiver 104 and configured to generate a vibratory signal. A signal transmitted from a transmitter, e.g. a wireless signal, and received by receiver 104 can be communicated to vibratory actuator 108 to generate a vibratory signal, wherein the vibratory signal can be applied to holding structure 106 and thereby any stem cells SC, such as MSC, within holding structure 106. In some aspects, implantable bioreactor IB can further comprise monitoring component 110 for monitoring the differentiation of the stem cells as discussed above.

As depicted in FIG. 2, implantable bioreactor IB can comprise a housing 202 made of one or more materials suitable for implantation and/or surgical placement in a tissue, e.g. subcutaneous surgical implantation. Housing 202 can comprise for example a silicone material. Housing 202 can also comprise in some embodiments titanium, such as for example in screws, fastening devices and or plates as components of housing 202. Housing 202 can comprise a substantially disc-shaped structure containing within it receiver 104, holding structure 106, vibratory actuator 108, and monitoring component 110. Implantable bioreactor IB can have a width W of about 1 cm, about 2 cm, about 4 cm, about 6 cm, about 8 cm, about 10 cm, about 12 cm or about 20 cm. Implantable bioreactor IB can have a thickness (i.e. depth of a disc-shaped structure) of about 0.5 cm, about 1 cm, about 2 cm, about 3 cm, about 4 cm, about 5 cm, or about 6 cm.

In embodiments where the bioreactor is implantable, implantation may be either in an animal host in which tissues are to be grown for later transplantation into a human, or directly into a human subject. Where a bioreactor as disclosed herein is to be implanted into a subject, a preferred subject is a vertebrate subject. An example of a vertebrate is a warm-blooded vertebrate. An example of a warm-blooded vertebrate is a mammal. An example of a mammal is a human. Additionally, as used herein, the term "patient" can include both human and animal patients, and thus, veterinary therapeutic uses are contemplated in accordance with the presently disclosed subject matter.

Provided is the treatment and/or use of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also contemplated is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, provided is the treatment of livestock, including, but not limited to, domesticated swine (pigs and hogs), ruminants, horses, poultry, and the like.

In some aspects an implantable bioreactor as disclosed herein can comprise a number of advantageous features, including for example, its small size and weight, and its use of lithium rechargeable batteries as a power source.

After implantation, an implantable bioreactor (IB) as disclosed herein can receive both recharge power and bi-directional data by way of wireless devices. Thus, the IB can remain implanted without the need for wires to penetrate through the skin of the subject in which it is implanted. Once implanted, the batteries of the IB can be recharged by inductive coupling. During implantation, data can be exchanged by way of a wireless bidirectional data link (BDL) with equipment outside the body, i.e., external equipment (EE). The BDL can be by any suitable means, such as for example, by using bluetooth RF wireless technology, a Body Area Network (BAN), or by infra-red technology (IR communication). In some aspects, IR communication may be optimal from a physical size and power consumption standpoint.

In some aspects, while implanted the BDL remains in low-power stand-by mode to conserve power. An IB can then use a micro power (nano-watt) on-board internal timer to determine when to "wake up", or become activated, to carry out scheduled tasks. Alternatively, in some embodiments, a signal from the EE "wakes up" or activates the IB to initiate BDL communication for either scheduled or unscheduled events.

Unscheduled events can include external user checks on device function, externally-initiated changes in the operational parameters or protocols, data transfer to the EE from the IB, etc. Timed events can include regular device self-test protocols, scheduled experimental interventions, scheduled experimental measurements, local non-volatile data logging, and taking physiologic or other measurements of the tissue with which the IB interacts.

These events also may include feedback-controlled interaction between the tissue and the IB, to enable the IB to take non-destructive real-time measures of tissue physiology, function (other signal) and utilize these signals in feedback-control to guide the tissue phenotype to the desired outcome. For example, in some aspects an IB can be used to generate bone tissue, in which case a good physiologic measure of bone tissue is the material stiffness. In general MSCs embedded in a scaffold will begin as a very limp structure with low stiffness, but as the phenotype progresses toward bone the stiffness of the tissue will increase over time. Feedback control can in some embodiments be important since at different stages of development it is likely that different stimulation protocols may need to be employed to optimize tissue phenotypic outcome. For example, in some aspects a lower frequency, higher displacement amplitude protocol may work best for freshly seeded MSC/scaffold tissue constructs, but as the tissue moves gradually toward the bone phenotype, it may be necessary and appropriate to change the stimulation parameters to higher frequency and/or lower displacement amplitude. To make these decisions, in some aspects the embedded microcontroller will have an onboard "expert system" (ES) that takes measurements of the tissue stiffness at specified intervals, stores this data for later upload to the EE, and uses the data in real time without requiring external intervention to apply appropriate signals to the tissues based on their measured developmental state and the desired phenotypic outcome.

In some embodiments, a computer readable medium is provided as part of an implantable bioreactor (in vivo), a controller (ex vivo), or both. The computer readable medium can have stored thereon executable instructions that when executed by the processor of a computer control the computer to perform steps comprising causing a transmitter to transmit a desired signal to a receiver, processing a returned signal from the receiver to the transmitter, and adjusting a signal transmitted by the transmitter to the receiver based on the returned signal. In some aspects, an output, such as for example data, can be provided to a user. In some aspects, the output can be displayed on a display unit such as a monitor or screen.

In Vitro Bioreactor Systems

In some embodiments a bioreactor system 300 as illustrated in FIG. 3 can be used to engineer a tissue as disclosed herein. In some embodiments, a bioreactor system 300 can comprise a stationary stage 302, a translatable stage 304, a cell culture vessel 306 and a controller 308 for controlling translatable stage 304, as depicted in FIG. 3.

In some embodiments, stationary stage 302 and translatable stage 304 are mounted to a base plate 310. Stationary stage 302 can be mounted to base plate 310 by frame 320. Stationary stage 302, translatable stage 304, base plate 310 and frame 320 can be constructed of any suitable material, e.g. plastic, that is durable and sufficiently rigid to support the structure of bioreactor system 300. By way of example and not limitation, stationary stage 302, translatable stage 304, base plate 310 and frame 320 can be constructed of acrylic, such as for example laser cut black acrylic, and can be solvent welded using dichloromethane. Each of these components can comprise materials, or all of the same material. In some embodiments stationary stage 302 and translatable stage 304 can be spaced apart a desired distance, such as for example about 1 cm apart, about 2.5 cm apart, or about 5 cm apart. In some embodiments, translatable stage 304 can have any desired dimensions depending on the application and number of cultures and/or the size and number of cell culture plates/containers, such as for example about 5 cm×10 cm, or about 7 cm×about 12 cm. For example, a larger stage 304 could in some embodiments provide for the ability to test more culture plates, and thereby more cell conditions.

Translatable stage 304 can be affixed to base plate 310 by wire 322. Wire 322 can be a wire or other flexible material sufficiently strong to support and/or suspend translatable stage 304 above base plate 310, yet flexible enough to allow for translational movement in translatable stage 304. For example, in some aspects wire 322 can comprise four or more lengths of alloy 402 stainless steel wire. In some embodiments the wire 322 can be about 2, 4, 6, 8, 10, 12, 14, 16, 18 or 20 cm long, and can have a diameter of about 0.02, 0.04, 0.06, 0.08 or 0.10 cm. In some embodiments, wire 322 can be about 7.6 cm long and have a diameter of about 0.051 cm.

In some embodiments, bioreactor system 300 further comprises an electromechanical voice coil actuator (VCA) 312 configured to linearly translate vibratory signals, movement or motion to translatable stage 104. Electromechanical VCA 312 can be mechanically linked to translatable stage 304 by translation member 314. Translation member 314 can comprise a thin strip of acrylic to serve as a flexible drive linkage. VCA 312 can be secured to stationary stage 302 using nylon thumbscrews or any other suitable securing mechanism.

Since translatable stage 304 can be affixed to base plate 310 by wire 322 any vibratory signal, movement, motion or any other linear translation translated by electromechanical VCA 312 is distributed throughout translatable stage 304, including cell culture vessel 306.

In some embodiments, linear translation of translatable stage 304 by VCA 312 can cause translatable stage 304 to be translated approximately within a plane for small displacements by applying horizontal forces, which in turn can deform wires 322 as the translatable stage 304 is displaced from its neutral resting point. Wires 322 can also provide a gentle restoring force which can assist in keeping translatable stage 304 in the center of its plane of motion. In some embodiments, VCA 312 can be configured to drive cell culture vessel 306 in a linear trajectory within the allowable plane of motion of translatable stage 304. In some aspects, the edges of translatable stage 304 can be cut or designed to facilitate securement of cell culture vessel 306, e.g. culture plates, with straps, rubber bands or other securing members.

In some embodiments, cell culture vessel 306 is mounted on a portion of translatable stage 304, wherein linear translation of the translatable stage 304 causes a linear translation of the cell culture vessel 306. In some embodiments, cell culture vessel 306 can be configured to allow for the culturing of cells in a liquid medium, wherein translation of translatable stage 304 can cause a fluid motion that transduces a mechanical shear force on the cultured cells. In some embodiments, cell culture vessel 306 can comprise a cell culture plate, for example a multi-well culture plate, that can be secured or attached to translatable stage 304.

In some embodiments, VCA 312 can directly apply mechanical strain to cells or tissues to be engineered, or to the substrate material upon which the cells or tissues are cultured. The degree of flexibility in how bioreactor system 300 can be configured and attached to culture vessels, synthetic substrates, or directly to tissues/cells themselves allows it to be employed for a wide array of tissue engineering applications.

In some embodiments, controller 308 for controlling translatable stage 304 comprises a computer, processor and computer readable medium having stored thereon executable instructions that when executed by the processor of the computer cause controller 308 to control the linear translation of the translatable stage through actuation and control of electromechanical voice coil actuator 312.

In some embodiments, the instrumentation of VCA 312, the embedded electronics[5] and the computer intermediary board[6] have been described elsewhere and are incorporated herein by reference. Briefly, an operator can select desired stimulation protocol parameters on a computer user interface written for this purpose in, for example, Visual Basic 2010. The parameters can then be sent via USB to an intermediary control board where they can be distributed to the appropriate bioreactor within the incubator via I2C digital communication, for example.

In some embodiments, the dynamic mechanical behavior, e.g. oscillatory behavior, of bioreactor system 100 can be modeled using the equations of motion describing an ordinary harmonic oscillator:

$$m\frac{d^2x}{dt^2} + c\frac{dx}{dt} + kx = 0, \quad \text{(Equation 1)}$$

where m is the mass, x is the linear position, c is the damping coefficient, k is the spring constant, and t represents time. The solution to this equation yields the following relationships that allow it to be expressed in terms of the natural frequency, $\omega_n$ and the damping ratio, $\zeta$:

$$\omega_n = \sqrt{k/m} \quad \text{(Equation 2)}$$
$$c_{critical} = 2\sqrt{km} = 2m\omega_n$$
$$\zeta = \frac{c}{c_{critical}},$$

which can be expressed as:

$$\frac{d^2x}{dt^2} + 2\zeta\omega_n\frac{dx}{dt} + \omega_n^2 x = 0.$$

As depicted in the above equations, the natural resonance of the system is a function of both the oscillating mass and the spring constant. The range of under-damped natural resonance frequencies for a bioreactor system 300 can be between about 5 and 7 Hz, as measured with an optical displacement sensor and an oscilloscope.

In some embodiments, bioreactor system 300 can further comprise an adjustable damping mechanism 324, as depicted in FIGS. 1, 2A and 2B. At stimulation frequencies close to that of the resonance of bioreactor system 300 or related harmonics, the amplitude of the resonance oscillations can become significant. Thus, to reduce resonant movement which is superimposed on the desired oscillatory motion, the damping coefficient can be adjusted using damping mechanism 324 that in some aspects can implement principles similar to those of magnetic braking[7]. The exemplary adjustable damping mechanism 324 illustrated in FIG. 2B comprises a magnet 402, such as for example a 1.91 cm square neodymium magnet, mounted to the underside of translatable stage 304. As magnet 402 passes over a non-magnetic electrical conductor 404, the induced electrical currents in conductor 404 can induce internal eddy currents that then can give rise to a magnetic field that opposes the motion of magnet 402 and therefore translatable stage 304. The opposing magnetic field can be proportional to the velocity of motion of magnet 402 with respect to non-magnetic conductor 404. This can result in a zero-hysteresis and nearly ideal linear damper.

In some embodiments, non-magnetic conductor 404 can comprise a machined block of aluminum with a press fit aluminum cylinder 406. Aluminum cylinder 406 can slide vertically into an appropriately machined Delrin cylinder 408 and can be held in place with a screw, bolt, pin or other securing member 410, such as a nylon (10-32) screw. Note that in FIG. 2A the non-magnetic conductor 404 and aluminum cylinder 406 are removed to test the effects when no damper is in place. In some embodiments, the machined block of aluminum can have dimensions as desired and as suitable for placement under translatable stage 304, such as for example 5.08 cm×5.08 cm×1.27 cm. Likewise, press fit aluminum cylinder 406 can have dimensions as desired and as suitable for sliding vertically into cylinder 408, such as for example 2.54 cm×1.59 cm diameter. Likewise, cylinder 408 can have dimensions as desired and as suitable for receiving press fit aluminum cylinder 406, such as for example 3.81 cm×2.54 cm diameter.

An adjustable damping mechanism 324 as described above and as illustrated in FIGS. 4A and 4B can permit the damping ratio to be adjusted manually to tune the dynamics of the system. For example, the closer the aluminum block is to the magnet, the higher the damping ratio. The use of very powerful grade N42 rare earth element magnets can also allow for a wide range of damping ratios to be achieved.

FIGS. 4C-4F depict the damping effect by comparing oscilloscope readings of the optoelectronic displacement sensor without the damper in place (FIGS. 4A, 4C and 4E) and with the damper in place (FIGS. 4D and 4F). The efficacy of an adjustable damper mechanism 324 can be quantified in each position by calculating the damping ratio of the harmonic system. If the system is underdamped, the damping ratio can be determined from the amplitudes of two successive peaks, $A_0$ and using $A_1$ the logarithmic decrement method[9]:

$$\zeta = \frac{1}{\sqrt{1 + \left(\frac{2\pi}{\ln(A_0/A_1)}\right)^2}}.$$

Because the system is designed to oscillate, the target damping ratio can still be less than the critically damped ratio of one. Using the adjustable damping mechanism depicted in FIG. 4B the damping ratio can be adjusted from $\zeta=0.01$ to $\zeta=0.15$.

In some embodiments a desired waveform can be generated by creating a graphical user interface using a software program such as Visual Basic for selection of waveform parameters. For example, a sinusoidal vector can be created using the following equation: $y = A*10 \sin(2\pi ft)$. The linear displacement of the platform from the zero position is represented by (y) and is measured by optical displacement sensor increments (about 1 micron). The Boolean selection of the sine waveform, the amplitude (A) in increments of 10 microns and the frequency in hertz (f) can be sent to controller 308 for controlling translatable stage 304. Before beginning the protocol, the sinusoid can be calculated on controller 308 for one complete period using a time increment of:

$$\frac{\text{Period}}{1000}$$

in order to yield exactly 1,000 steps per sine wave. The sine wave can in some embodiments be repeated successively for the duration of the stimulus. Frequency can then be set by establishing the update period for the sinusoidal function such that the waveform amplitude can be updated at 1,000 times the desired frequency of the output sinusoid. Waveform parameters can be stored on and executed by controller 308 for controlling translatable stage 304 to thereby implement the desired waveform and impart upon the cultures the desired vibrational signal.

In some embodiments a stimulation protocol can be designed and implemented by a bioreactor system 300 to stimulate and/or impact differentiation of stem cells in culture (or in vivo as discussed herein) to thereby engineer a tissue. In some embodiments, to avoid over-stressing the cells and thereby disrupting the cell cycle, a stimulation protocol can be set to include intervals of stimulation coordinated with intervals of rest, for example 15 minutes of rest between each 1 minute stimulus duration. Stimulation protocols for a bioreactor system 300 can be designed to provide stimuli ranging from 1 Hz stimulus up to 100 Hz. Vibratory signals can be introduced to MSCs in vitro and/or in vivo to cause differentiation toward specific phenotypes and/or to generate a desired tissue. At lower frequencies (about 1 Hz) a cartilage phenotype can be generated, while at higher frequencies (about 100 Hz) a bone phenotype can be generated. Along the range of frequencies from about 1 Hz to about 100 Hz other engineered tissue types can be generated. For example, between about 1 Hz and about 50 Hz fibrocartilage can be engineered, and between about 50 Hz and 100 Hz a hypertrophic cartilage can be engineered. Thus, in some embodiments a stimulation protocol can comprise vibratory signals of about 1 Hz, 5 Hz, 10 Hz, 20 Hz, 30 Hz, 40 Hz, 50 Hz, 60 Hz, 70 Hz, 80 Hz, 90 Hz, 100 Hz, intermediates thereof, and/or combinations thereof. Waveform amplitudes can be adjusted to apply similar levels of energy at each frequency.

Stem Cell Differentiation

In some embodiments tissues can be engineered and/or cells can be caused to differentiate to desired cell types using undifferentiated cell types such as for example stem cells. In some embodiments, mesenchymal stem cells (MSC) can be used in the disclosed methods, apparatuses, devices and systems. In some embodiments, MSCs can be human umbilical cord (hUC)-derived MSCs. In some embodiments, the MSCs can be porcine umbilical cord (pUC)-derived MSCs. In some embodiments, MSCs can be sourced from other animals such as for example mice, rats, monkeys, apes, etc., and can be used for medical, therapeutic, regenerative and/or experimental purposes.

Once harvested and prior to exposure to vibratory signals, mechanical influences, or other signals to cause differentiation, MSCs can in some embodiments, and particularly in vitro applications, be cultured such as discussed in the Examples. By way of example and not limitation, for osteogenesis either hUC or pUC MSCs can be seeded at about $2\times10^4$ cell/cm$^2$ and incubated in a culture medium such as MEM, which can be supplemented with for example FBS, glutamine, Penicillin/Streptomycin, b-glycerophosphate, dexamethasone, and/or ascorbic acid. Medium can be replaced every 1-5 days, or for example every 2 days. Other cell densities can be used for seeding without departing from the scope of the instant disclosure, so long as there are sufficient cells for survival and no too many that would overgrow the conditions. More particularly, and by way of example and not limitation, for osteogenesis MSCs can be seeded at about $2\times10^4$ cell/cm$^2$ and incubated in MEM supplemented with 10% FBS, 2 mM glutamine, 100 U/mL/ 100 µg/mL Penicillin/Streptomycin, 10 mM b-glycerophosphate, 0.1 µm dexamethasone, and 50 µM ascorbic acid. By way of example and not limitation, for chondrogenesis either hUC or pUC MSCs seeded at a density of $4\times10^5$ cells/cm$^2$ and incubated in a culture medium such as (DMEM)-high glucose supplemented with ITS-1, ascorbic acid, dexamethasone, transforming growth factor (TGF)-β1, TGF-β3, insulin-like growth factor (IGF)D and/or L-proline. More particularly, and by way of example and not limitation, for chondrogenesis either hUC or pUC MSCs seeded at a density of $4\times10^5$ cells/cm$^2$ and incubated in (DMEM)-high glucose supplemented with ITS-1, 0.1 mM ascorbic acid, $10^{-7}$M dexamethasone, 10 ng/mL transforming growth factor (TGF)-β1, 10 ng/mL TGF-β3 100 ng/mL insulin-like growth factor (IGF)D and 40 µg/mL L-proline.

To assess MSC differentiation before, during and/or after exposure to vibratory signals, mechanical influences, or other signals to cause differentiation and tissue engineering, stem cells can be visualized and analyzed using a staining methodology, and/or gene expression profiles can be analyzed. For example, osteoblastogenic differentiation can be assayed using alizarin red staining, at 21 days for example. Chondrogenic differentiation can be assayed using alcian blue staining, at 21 days for example.[11] The alizarin red allows for the detection of calcium deposits in osteogenic induction, while the alcian blue allows for the detection of the presence of glycosaminoglycans and mucopolysaccharides in chondrogenic induction. After removal of excess dye by washing with distilled water, the stained cultures can be analyzed under light microscopy.

To analyze expression of genes involved in MSC osteogenic differentiation, the total cellular RNA can be isolated as is known in the art, such as for example using the RNeasy total RNA extraction kit from Qiagen. Real-time fluorescent quantitative PCR can be performed as is known in the art, such as for example by using an ABI PRISM 7700 (Applied Biosystems), and using primers sequenced for the listed genes (see, e.g. Table 2 in the Examples). More particularly, an osteogenic lineage can be indicated by increases of BMP2 levels. Comparatively, a chondrogenic lineage can be indicated by increases in COL2/COL1.

Thus, in some embodiments vibratory signals can be introduced to MSCs in vitro and/or in vivo to cause differentiation toward specific phenotypes and/or to generate a desired tissue. At lower frequencies (about 1 Hz) a cartilage phenotype can be generated, while at higher frequencies (about 100 Hz) a bone phenotype can be generated. Along the range of frequencies from about 1 Hz to about 100 Hz other engineered tissue types can be generated. For example, between about 1 Hz and about 50 Hz fibrocartilage can be engineered, and between about 50 Hz and 100 Hz a hypertrophic cartilage can be engineered. Unlike previous studies that have focused on relative amounts of bone or cartilage differentiation markers, the instant disclosure tracks comprehensive gene expression profiles. Additionally, prior studies have only applied compressive loads to the samples.

If done in vivo, such as for example using an implantable bioreactor as disclosed herein, the application of vibratory signals can be delivered at a particular site in a patient or subject to cause differentiation of MSC and to generate a desired cell type and/or tissue.

Methods and Treatments

Figure 5:
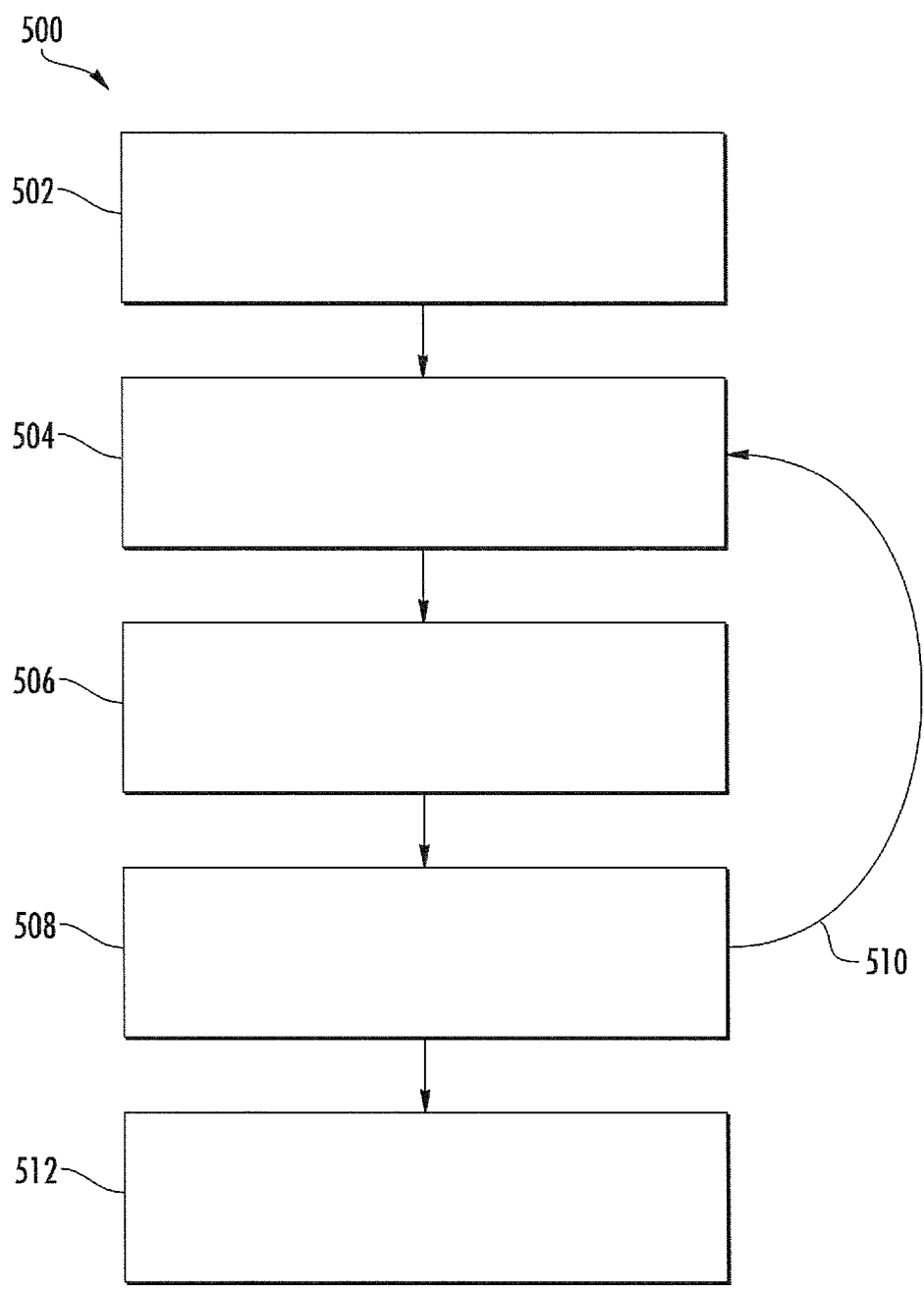
FIG. 5 is a flow diagram of a method of tissue engineering.

In some embodiments methods of engineering a tissue are provided. In some embodiments such methods can comprise providing mesenchymal stem cells (MSC), applying a vibratory signal of a desired frequency to the MSC, monitoring a MSC differentiation response, and, if necessary, adjusting the vibratory signal applied to MSC based on the MSC differentiation response, whereby a desired tissue is engineered from the MSC. Such a method 500 is depicted in FIG. 5, wherein MSCs are provided in step 502 and a vibratory signal of a desired frequency is applied in step 504. In step 506 MSC differentiations is monitored. If necessary, depending on results indicated by the monitoring of differentiation in step 506, and depending on the desired cell type and/or tissue phenotype, the vibratory signal applied to MSC can be adjusted in step 508 and a feed-back signal 510 can be provided to the frequency application step 504. This closed-loop tissue engineering approach can be continued until the desired tissue is engineered in step 512.

In some embodiments, feed-back signal 510 can indicate that the vibratory signal of a desired frequency as applied in step 504 should continue and not be adjusted based on the MSC differentiation or lack thereof, while in some embodiments feed-back signal 510 can indicate that the vibratory signal of a desired frequency as applied in step 504 should change based on the stage of MSC differentiation. In some embodiments adjusting the vibratory signal applied to the MSC based on the MSC differentiation response can comprise increasing or decreasing the frequency of the vibratory signal, and/or changing the amplitude, waveform, duration and/or intermittence of the vibratory signal. In some aspects, the vibratory signal of a desired frequency can be applied to the MSC over a series of intermittent time intervals.

In some embodiments, the methods as disclosed herein can comprise harvesting stem cells, such as MSC, from a subject and culturing them in vitro. In some embodiments, the MSCs can be cultured are in vivo.

In some embodiments, the applied vibratory signal can have a frequency ranging from about 0.1 hertz to about 1,000 hertz, wherein applying a vibratory signal with a frequency ranging from about 0.1 hertz to about 50 hertz induces chondrogenesis in the MSC. When chondrogenesis is induced the desired and/or resulting tissue can comprises a cartilage phenotype. Alternatively, applying a vibratory signal with a frequency ranging from about 50 hertz to about 1,000 hertz can induce osteogenesis in the MSC. When osteogenesis is induced the desired and/or resulting tissue can comprises a bone phenotype.

In some embodiments, monitoring MSC differentiation response in the disclosed methods can comprise assessing a tissue forming from MSC for: tissue density, calcium concentration, glycosaminoglycan concentration, mucopolysaccharide concentration, gene expression profiles, and/or combinations thereof.

In some embodiments, the methods disclosed herein can be performed in vivo in a subject. In some embodiments, the disclosed methods can be performed in vitro and the resulting engineered tissue can be implantable in a subject. The subject is a human subject, or an animal subject. In some aspects, the MSCs can be of human origin and the subject can be an animal subject, wherein a desired tissue can be grown in the animal subject and later transplanted into a human subject for surgical correction of a defect or injury.

The subject matter disclosed herein can be implemented in software in combination with hardware and/or firmware. For example, the subject matter described herein can be implemented in software executed by a processor. In one exemplary implementation, the subject matter described herein can be implemented using a computer readable medium having stored thereon computer executable instructions that when executed by a processor of a computer control the computer to perform steps. Exemplary computer readable mediums suitable for implementing the subject matter described herein include non-transitory devices, such as disk memory devices, chip memory devices, programmable logic devices, and application specific integrated circuits. In addition, a computer readable medium that implements the subject matter described herein can be located on a single device or computing platform or can be distributed across multiple devices or computing platforms.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a" and "an" mean "one or more" when used in this application, including the claims.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed as a "p value". Those p values that fall below a user-defined cutoff point are regarded as significant. In some embodiments, a p value less than or equal to 0.05, in some embodiments less than 0.01, in some embodiments less than 0.005, and in some embodiments less than 0.001, are regarded as significant. Accordingly, a p value greater than or equal to 0.05 is considered not significant.

As used herein, the term "subject" refers to any organism for which application of the presently disclosed subject matter would be desirable. The subject treated in the presently disclosed subject matter in its many embodiments is desirably a human subject, although it is to be understood that the principles of the presently disclosed subject matter indicate that the presently disclosed subject matter is effective with respect to all vertebrate species, including mammals, which are intended to be included in the term "subject". Moreover, a mammal is understood to include any mammalian species in which treatment of a tumor and/or a cancer is desirable, particularly agricultural and domestic mammalian species.

EXAMPLES

The following examples provide exemplary, non-limiting embodiments of the presently disclosed subject matter. In light of the present disclosure and the general level of skill in the art, those of skill will appreciate that the following Examples are intended to be exemplary only and that numerous changes, modifications, and alterations can be employed without departing from the scope of the presently claimed subject matter.

Example 1

Bioreactor Frame Construction

A bioreactor system is illustrated in FIG. 3. By way of example and not limitation, the frame was constructed primarily of laser cut 0.635 cm black acrylic and was solvent welded using dichloromethane. In this example the assembly consisted of a stationary stage and a translatable stage spaced about 2.5 cm apart and mounted to a baseplate (33.0 cm×7.6 cm).

The reciprocating stage of the mechanobioreactor in this example consisted of an acrylic platform (7.6 cm×12.7 cm) suspended by four lengths of alloy 402 stainless steel wire (7.6 cm long×0.051 cm diameter). Linear translation was achieved similarly to a dual four bar linkage driven by an electromechanical voice coil actuator (VCA). The movable stage was translated approximately within a plane for small displacements by applying horizontal forces, which in turn deformed the long and thin support wires as the moveable stage was displaced from its neutral resting point. The support wires also provided a gentle restoring force which tended to keep the moveable stage in the center of its plane of motion. In this example the VCA was configured to drive the culture plate in a linear trajectory within the allowable plane of motion of the moveable stage. The edges of the moveable stage were cut to facilitate securement of culture plates with straps or rubber bands. The VCA mechanism was secured to the stationary platform using nylon thumbscrews. A thin strip of acrylic was used to attach the VCA to the movable stage to serve as a flexible drive linkage.

In this example the horizontal motion of the culture plate driven by the VCA caused fluid motion back and forth across the cells in culture at the bottom of each well. In this configuration it was the fluid motion that transduced mechanical shear forces to the cells in culture. In other configurations as disclosed herein the VCA directly applied mechanical strain to engineered tissues, or to the substrate material upon which the tissues were cultured.

Example 2

Electronics and Voice Coil Actuator

The instrumentation of the voice coil linear actuator, the embedded electronics[6] and the computer intermediary board[6] have been described elsewhere and are incorporated herein by reference. Briefly, an operator can select desired stimulation protocol parameters on a computer user interface written for this purpose in, for example, Visual Basic 2010. The parameters can then be sent via USB to an intermediary control board where they can be distributed to the appropriate bioreactor within the incubator via I2C digital communication, for example.

The voice coil actuator employed here operated by Lorentz forces generated within an electric coil in a direction orthogonal to a static magnetic field.[7] The coil was mounted within a compliant mechanism spring with very low hysteresis and low spring constant such that by varying the direction and magnitude of the current in the coil, the linear position can be controlled over a displacement of about +/−2 mm from the neutral position. The VCA position was tracked with sub-micron precision using an optoelectronic differential displacement sensor fitted with an optical beam interrupter.[8] The embedded microcontroller monitored the position of the actuator and controlled the current through the coil in accordance with the programmed stimulus protocol.

Example 3

Oscillatory Behavior

The dynamic mechanical behavior of this system was modeled using the equations of motion describing an ordinary harmonic oscillator:

$$m\frac{d^2x}{dt^2} + c\frac{dx}{dt} + kx = 0, \quad \text{(Equation 1)}$$

where m is the mass, x is the linear position, c is the damping coefficient, k is the spring constant, and t represents time. The solution to this equation yields the following relationships that allow it to be expressed in terms of the natural frequency, $\omega_n$ and the damping ratio, $\zeta$:

$$\omega_n = \sqrt{k/m} \quad \text{(Equation 2)}$$
$$c_{critical} = 2\sqrt{km} = 2m\omega_n$$
$$\zeta = \frac{c}{c_{critical}},$$

which can be expressed as:

$$\frac{d^2x}{dt^2} + 2\zeta\omega_n\frac{dx}{dt} + \omega_n^2 x = 0.$$

As depicted in the above equations, the natural resonance of the system is a function of both the oscillating mass and the spring constant. The range of under-damped natural resonance frequencies in the experiments presented here was measured with the optical displacement sensor and an oscilloscope to be between 5 and 7 Hz.

Example 4

Adjustable Damping Mechanism

At stimulation frequencies close to that of the resonance of the system or related harmonics, the amplitude of the resonance oscillations becomes significant. To reduce resonant movement which is superimposed on the desired oscillatory motion, the damping coefficient was adjusted using a mechanism that implements principles identical those of magnetic braking[7]. An exemplary adjustable damping mechanism is illustrated in FIG. 2. A 1.91 cm square neodymium magnet was mounted to the underside of the translation platform. As the magnet passed over a nonmagnetic electrical conductor, the induced electrical currents in the conductor induced internal eddy currents that then gave rise to a magnetic field that opposes the motion of the permanent magnet and therefore the translation stage. The opposing magnetic field was proportional to the velocity of motion of the permanent magnet with respect to the non-magnetic conductor. This resulted in a zero-hysteresis and nearly ideal linear damper.

The nonmagnetic conductor was a machined block of aluminum 5.08 cm×5.08 cm×1.27 cm with a press fit aluminum cylinder 2.54 cm×1.59 cm diam. The aluminum cylinder slid vertically into an appropriately machined Delrin cylinder (3.81 cm×2.54 cm diameter) and was held in place with a nylon (10-32) screw. This arrangement allowed the damping ratio to be adjusted manually to tune the dynamics of the system: the closer the aluminum block was to the magnet, the higher the damping ratio. The use of very powerful grade N42 rare earth element magnets allowed a wide range of damping ratios to be achieved.

The efficacy of the adjustable damper mechanism was quantified in each position by calculating the damping ratio of the harmonic system. Since the system was underdamped, the damping ratio was determined from the amplitudes of two successive peaks, $A_0$ and $A_1$ using the logarithmic decrement method[9]:

$$\zeta = \frac{1}{\sqrt{1 + \left(\frac{2\pi}{\ln(A_0/A_1)}\right)^2}}.$$

Because the system was designed to oscillate, the target damping ratio was still less than the critically damped ratio of one. Using the adjustable damping mechanism depicted in FIG. 2 the damping ratio was adjusted from $\zeta=0.01$ to $\zeta=0.15$.

Example 5

Waveform Generation

A graphical user interface was created in Visual Basic 2010 for selection of wave form parameters. A sinusoidal vector was created on the embedded PIC18F4550 microcontroller using the following equation:

$$y = A*10 \sin(2\pi ft).$$

The linear displacement of the platform from the zero position is represented by (y) and is measured by optical displacement sensor increments (about 1 micron). The Boolean selection of the sine waveform, the amplitude (A) in increments of 10 microns and the frequency in hertz (f) were sent to the bioreactor microcontroller via the electronics described above. Before beginning the protocol, the sinusoid was calculated on the microcontroller for one complete period using a time increment of:

$$\frac{\text{Period}}{1000}$$

in order to yield exactly 1,000 steps per sine wave. The sine wave was repeated successively for the duration of the stimulus. Frequency was then set by establishing the update period for the sinusoidal function such that the waveform amplitude was updated at 1,000 times the desired frequency of the output sinusoid.

Example 6

Stimulation Protocol

To avoid over-stressing the cells and thereby disrupting the cell cycle, the stimulation protocol was set to allow 15 minutes of rest between each 1 minute stimulus duration. Two bioreactors were set up in parallel, one with 1 Hz stimulus and the other with 100 Hz. Waveform amplitudes were adjusted to apply similar levels of energy at each frequency.

Example 7

Umbilical Cord Harvest

Human umbilical cord (hUC)-derived mesenchymal stem cells (MSCs) were obtained from human UCs following appropriate consent and cells were isolated from tissue explants, as previously described.[10] Briefly, UCs were cut from the placenta and immersed in sterile transport solution (PBS supplemented 300 U/mL penicillin, 300 µg/mL streptomycin). Approximately 6 cm sections were cut and washed to remove residual blood. The UC epithelium and vessels were removed and discarded, and the Wharton's Jelly was cut into 1 mm²-sized pieces and placed in Dulbecco Modified Eagle Medium (DMEM/F12) supplemented with 10% MSC-FBS, 50 µg/mL gentamicin, 100 U/mL penicillin, 100 µg/mL streptomycin, 55 µM β-Mercaptoethanol, and 1 mM Sodium Pyruvate. Growth medium was replaced every 3 to 4 days.

Porcine umbilical cord (pUC)-derived MSCs were obtained from pigs at the North Carolina State University Swine Education Unit, Raleigh, N.C., United States of America. The umbilical cords were processed as described for human cords with small variation. To prevent contamination, cords were dipped briefly in betadine followed by 70% ethanol before dissection as described for human cells. Isolated Wharton's Jelly was cut into approximately 1 mm²-sized pieces and placed in DMEM (supplemented with 15% FBS, 50 µg/mL gentamicin, 100 U/mL penicillin, 100 µg/mL streptomycin, and 0.25 µg/mL amphotericin B). Growth media was replaced every 2 or 3 days.

Example 8

Flow Cytometry

Cultured cells were trypsinized and resuspended at a concentration of $10^6$ cells/mL in blocking buffer (0.5% BSA, 0.01% Na-azide, 1×PBS). A total of $10^5$ cells were treated with 10 µL of diluted primary antibody (CD90$^+$, CD73$^+$, CD105$^+$, CD34$^+$, or SSEA-4$^+$) then incubated for 20 minutes on ice. After 3 washes with cold PBS, cells were incubated with 1.5 µg of secondary antibody in 100 µL of blocking buffer for 20 minutes on ice in the dark. Samples were then washed with PBS 3 times and fixed in 1% paraformaldehyde and stored at 4° C. in the dark until analysis. Cells were analyzed using a Beckman-Coulter (Dako) CyAn ADP and Summit 4.3 software. The results of this process can be seen in Table 1 below.

TABLE 1

| Marker | Mean % |
|---|---|
| Porcine | |
| CD105 | 89 |
| CD90 | 99 |
| CD73 | 71 |
| SSEA-4 | <1 |
| CD34 | <1 |
| Human | |
| CD105 | 98 |
| CD90 | 99 |
| CD73 | 97 |
| SSEA-4 | 65 |
| CD34 | <1 |

Example 9

Osteogenesis

Either hUC or pUC MSCs were seeded at $2 \times 10^4$ cell/cm² and incubated in-MEM supplemented with 10% FBS, 2 mM glutamine, 100 U/mL/100 µg/mL Penicillin/Streptomycin, 10 mM b-glycerophosphate, 0.1 µm dexamethasone, and 50 µM ascorbic acid. Medium was replaced every 2 days. Osteoblastogenic differentiation was assayed at 21 days by Alizarin Red staining.

Example 10

Chondrogenesis

Umbilical cord MSCs (UC-MSC; human or porcine) were seeded at a density of $4 \times 10^5$ cells/cm² an incubated in (DMEM)-high glucose supplemented with ITS-1, 0.1 mM ascorbic acid, $10^{-7}$M dexamethasone, 10 ng/mL transforming growth factor (TGF)-β1, 10 ng/mL TGF-β3 100 ng/mL insulin-like growth factor (IGF)D and 40 µg/mL L-proline. Chondrogenic differentiation was assayed at 21 days by alcian blue staining.[11]

Example 11

Vibration

UC-MSC were seeded in regular growth media, at either $2 \times 10^4$ cell/cm² (for 100 Hz) or $4 \times 10^5$ cells/cm² (for 1 Hz). Cells were allowed to attach for 24 hours and then transfer to vibratory bioreactor program for either 100 Hz or 1 Hz vibration. Cultures were subjected to vibration cycles, as described above, for 15 hours/day for a period of 10 days. Regular growth media was changed every 3 days.

Example 12

Differentiation Analysis

At 21 days post induction, cells were fixed in 10% buffered formalin for 30 minutes and rinsed with distilled water. To detect calcium deposits in osteogenic induction, cells were stained with 2% alizarin red S solution, pH 4.2, for 10 minutes; in chondroinduced cells the presence of glycosaminoglycans and mucopolysaccharides was demonstrated by staining with 0.1 mg/ml Alcian Blue 8 GX for 20 minutes. Excess dye was removed by careful washes with distilled water. Staining cultures were analyzed under light microscopy, using a Nikon Eclipse Ti—S inverted microscope.

Example 13

RT-PCR Analysis

To analyze expression of genes involved in MSC osteogenic differentiation, the total cellular RNA was isolated using the RNeasy total RNA extraction kit from Qiagen. Real-time fluorescent quantitative PCR was performed by using an ABI PRISM 7700 (Applied Biosystems) using specific primers sequence for the listed genes (Table 2). The ribosomal 18S RNA was used as an internal standard and the $2^{-\Delta\Delta CT}$ quantification method was used for data analysis.

experiments. Statistical analyses were performed using GraphPad Prism 5®. A two-way analysis of variance (ANOVA) test was used to determine significant differences between groups. Comparison between means was determined using the Bonferroni post-hoc test using a confidence level of 0.05.

TABLE 2

RT-PCR primers and probes

| | Human | Swine |
|---|---|---|
| BMP2 | | |
| Forward | CCA GAC CAC CGG TTG GAG A (SEQ ID NO: 1) | GGC TGG AGA GGG CAG CCA (SEQ ID NO: 13) |
| Reverse | TTC CAA AGA TTC TTC ATG GTG G (SEQ ID NO: 2) | CTC ATT TCT GGC AGT TCT TCC (SEQ ID NO: 14) |
| Probe | FAG CCA GCC GAG CCA ACA CTG TGC Q (SEQ ID NO: 3) | FTG GCC AAC ACC GTG CGC AGC TTC CAQ (SEQ ID NO: 15) |
| Col1A1 | | |
| Forward | AAC AGC CGC TTC ACC TAC AG (SEQ ID NO: 4) | GCC AAG AAG AAG ACA TCC CA (SEQ ID NO: 16) |
| Reverse | TCA ATC ACT GTC TTG CCC CA (SEQ ID NO: 5) | TTT CCA CAC GTC TCG GTC AT (SEQ ID NO: 17) |
| Probe | FTC GAT GGC TGC ACG AGT CAC ACC GQ (SEQ ID NO: 6) | FAG TCA CCT GCG TAC AGA ACG GCC TCQ (SEQ ID NO: 18) |
| Col2A1 | | |
| Forward | CAA TAG CAG GTT CAC GTA CAC (SEQ ID NO: 7) | TGT CAC GGC CAG GAT GTC CA (SEQ ID NO: 19) |
| Reverse | TCG ATA ACA GTC TTG CCC CA (SEQ ID NO: 8) | GGC TTC CAC ACA TCC TTA TCA (SEQ ID NO: 20) |
| Probe | FAG GAT GGC TGC ACG AAA CAT ACC GQ (SEQ ID NO: 9) | FAC CTC TGC CCA TCC TGC ACG CAG CQ (SEQ ID NO: 21) |
| 18S | | |
| Forward | AGA AAC GGC TAC CAC ATC CA (SEQ ID NO: 10) | AGA AAC GGC TAC CAC ATC CA (SEQ ID NO: 22) |
| Reverse | CTC GAA AGA GTC CTG TAT TGT (SEQ ID NO: 11) | CTC GAA AGA GTC CTG TAT TGT (SEQ ID NO: 23) |
| Probe | FAG GCA GCA GGC GCG CAA ATT ACQ (SEQ ID NO: 12) | FAG GCA GCA GGC GCG CAA ATT ACQ (SEQ ID NO: 24) |

F; 5'-Fluorescein (FAM) and 5'-Tetrachloro-Fluorescein (TET) in 18S.
Q; Quencher (TAMRA)

Example 14

Statistical Analysis

Experiments were run in two different cell lines to account for individual variations. Values are reported as mean±standard error of the mean (SEM) of four independent Results and Discussion of Examples 1-14

The bioreactor developed for these experiments successfully generated the desired waveform parameters. The 100 Hz and 1 Hz stimuli were experimentally measured to be exactly 100.0 Hz and 1.0 Hz respectively with zero frequency drift after 2 days of operation.

The frequency of stimulus had a pronounced effect on UC-MSC differentiation in both human and porcine models when compared to controls. Relative to the respective controls, the results of the human and porcine studies were similar. The positive control wells were chemically induced to promote osteogenesis or chondrogenesis. Alizarin red staining of the osteogenesis positive control showed a high calcium content as expected. Correspondingly, Alcian blue staining of the chondrogenesis positive control showed high levels of GAGs as expected. The negative control wells tended toward osteogenesis in this study with very little cartilage present after 10 days.

The samples driven at 100 Hz showed denser calcium deposits than negative controls in both human and porcine studies as well as very low levels of GAGs. The samples driven at 1 Hz demonstrated substantially higher GAG content than the negative controls and lower calcium content than the 100 Hz samples.

The results of the mRNA quantification experiment are presented in FIGS. 6A-6D. In both hUC-MSCs (FIG. 6A) and pUC-MSCs (FIG. 6B), the 100 Hz stimulus showed a significant increase in BMP2 levels when compared with the 1 Hz samples and the controls. Additionally, both hUC-MSCs (FIG. 6C) and pUC-MSCs (FIG. 6D) had significantly higher levels of COL2/COL1 after the 1 Hz stimulus than the 100 Hz samples and the controls.

The data generated in the above-disclosed Examples, and the instant disclosure, demonstrate that vibratory signals can be used to stimulate both human and porcine MSCs, including UC-MSCs, toward specific phenotypes. At lower frequencies a cartilage phenotype can be generated, while at higher frequencies a bone phenotype can be generated. Unlike previous studies that focused on relative amounts of bone or cartilage differentiation markers, the instant studies tracked comprehensive gene expression profiles. Additionally, prior studies that indicated chondrogenesis differentiation of MSCs applied only compressive loads to the samples.

The assessment from the alcian blue and alizarin red staining was reiterated quantitatively by measuring BMP2 and COL2/COL1 mRNA in the samples following the stimulus. This result supplies evidence that MSC differentiation is sensitive to vibrational frequency.

The results above support the development of implantable bioreactors as disclosed herein, and as tested in a subcutaneous porcine model. The stimulation paradigm of the implantable bioreactor was informed by the results of in vitro studies conducted with the system presented here.

A versatile bioreactor was constructed to enable research of the effects of vibrational stresses on MSCs in vitro. As a demonstrative example, human and porcine umbilical cord-derived MSCs were stimulated with the present bioreactor system at frequencies of 1 Hz and 100 Hz. The lower frequency (1 Hz) resulted in a cartilage-like phenotype for both human and porcine MSCs, whereas the higher frequency (100 Hz) resulted in bone-like phenotype, as indicated by expression of BMP2 and COL2/COL1 and by Alizarin Red and Alcian Blue staining.

Example 15

Implantable Bioreactor Analysis

Figure 7:
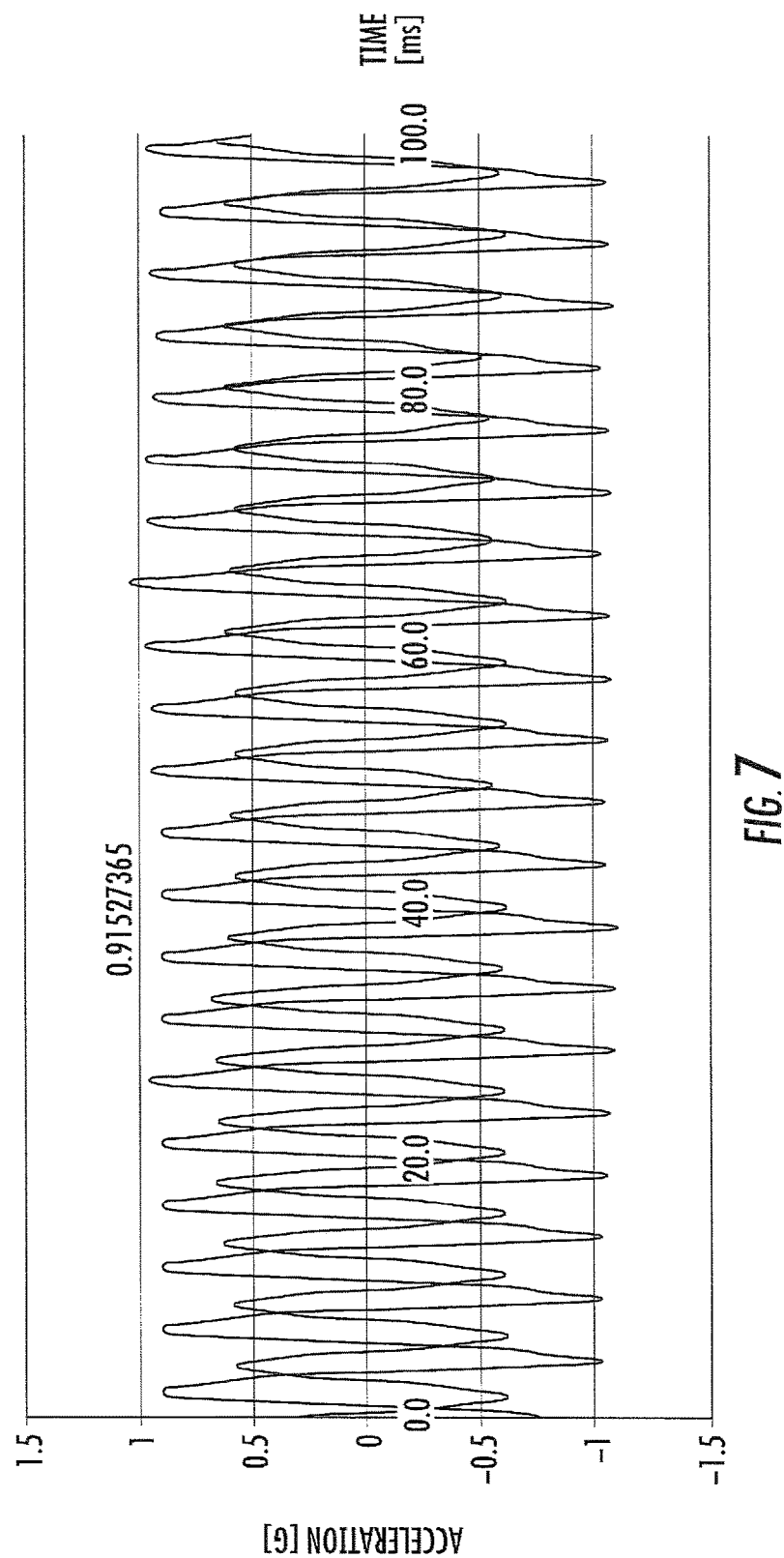
FIG. 7 is a graphical depiction of accelerometer data from an implantable bioreactor.

An implantable bioreactor as illustrated in FIGS. 1 and 2 and as discussed herein was develop and analyzed. FIG. 7 depicts and Table 3 provides accelerometer data from the analysis of an implantable bioreactor. In Table 1 "Unconstrained" refers to vibration of the implantable bioreactor when sitting at the bottom of a larger dish, while "Constrained" refers to the vibration of the implantable bioreactor with a wedge to hold the bioreactor in place in the larger dish.

TABLE 3

| Frequency | t1 | t2 | t2 − t1 | cycles | Hz |
|---|---|---|---|---|---|
| Unconstrained | 2.6 | 98.2 | 95.6 | 20 | 209.21 |
| Constrained | 1.0 | 98.2 | 97.0 | 20 | 206.19 |

Example 16

Analysis of MSC Differentiation in Implantable Bioreactor

Figure 8A:
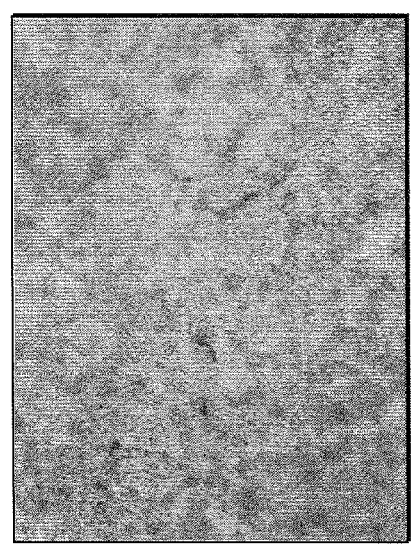
FIGS. 8A-8C are images of calcium stained MSCs after no vibration (FIG. 8A), vibration 1 h/d (FIG. 8B), and vibration 15 h/d (FIG. 8C)
Figure 8B:
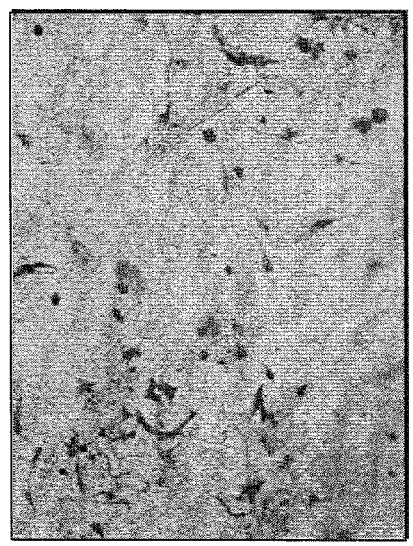
Figure 8C:
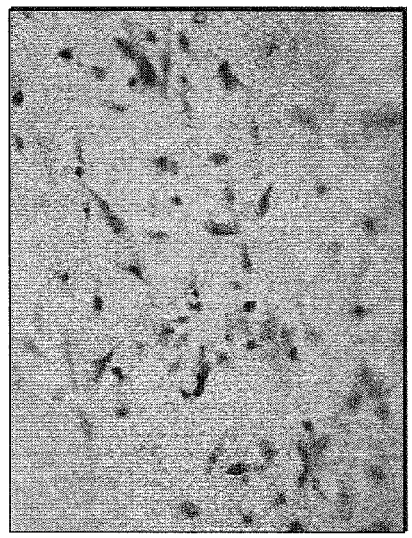
Figure 9:
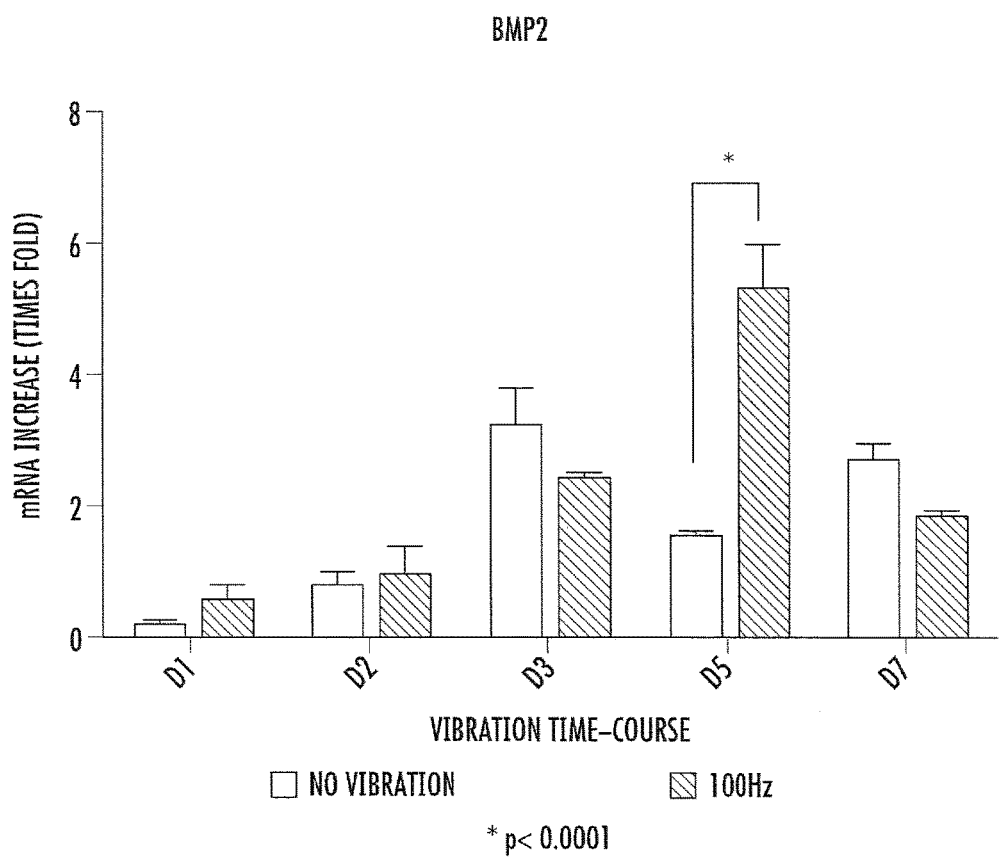
FIG. 9 is a graphical depiction of BMP2 gene expression in MSCs exposed to vibrational signals in vivo.

MSC were place in an implantable bioreactor as illustrated in FIGS. 1 and 2 and as discussed herein and exposed to vibrational frequencies. The results are depicted in FIGS. 8A-8C. FIG. 8A-8C show calcium stained MSCs after no vibration (FIG. 8A), vibration 1 h/d (FIG. 8B), and vibration 15 h/d (FIG. 8C). Images are shown at day 7, after 100 Hz of vibration for 30 seconds with 15 minute rest intervals. In FIG. 9 the BMP2 gene expression is shown for the same MSCs. At day 5 cells exposed to 100 Hz had significantly increased levels of BMP2.

REFERENCES

All references cited herein, including but not limited to patents, patent applications and publications thereof, scientific publications, database entries, and references available on the World Wide Web, are incorporated herein by reference to the extent that they supplement, explain, provide a background for, or teach methodology, techniques, and/or compositions employed herein.

[1] A. I. Caplan, "Adult Mesenchymal Stem Cells for Tissue Engineering Versus Regenerative Medicine," no. June, pp. 341-347, 2007.

[2] S. M. Richardson, J. a Hoyland, R. Mobasheri, C. Csaki, M. Shakibaei, and A. Mobasheri, "Mesenchymal stem cells in regenerative medicine: opportunities and challenges for articular cartilage and intervertebral disc tissue engineering.," *Journal of cellular physiology*, vol. 222, no. 1, pp. 23-32, Jan. 2010.

[3] A. Hilfiker, C. Kasper, R. Hass, and A. Haverich, "Mesenchymal stem cells and progenitor cells in connective tissue engineering and regenerative medicine: is there a future for transplantation?," *Langenbeck's archives of surgery/Deutsche Gesellschaft für Chirurgie*, vol. 396, no. 4, pp. 489-97, April 2011.

[4] A. C. Guyton and J. Edward, *Textbook of Medical Physiology*, 11th ed. Elsevier Inc., 2006, pp. 27-42.

[5] A. T. Cashion, B. Salazar, R. Birla, and R. G. Dennis, "Cyclic strain bioreactor for self organized cardiac patch tissue engineering." 2013.

[6] A. T. Cashion, D. K. Hubbard, K. Donnelly, O. Favorov, and R. G. Dennis, "A method of collecting and analyzing low-frequency dielectric absorption data for rapid algal oil yield assessment," 2013.

[7] D. Halliday, R. Robert, and J. Walker, *Electromagnetism and Optics*, 7th ed. John Wiley & Sons, Inc., 2006, pp. 764-816.

[8] R. G. Dennis, "Measurement of Pulse Propagation in single permeabilized muscle fibers by optical diffraction," University of Michigan, Ann Arbor, Mich., 1996.

[9] D. J. Inman, *Engineering Vibration*, 3rd ed. Pearson, 2008.

[10] M. Caballero, C. R. Reed, G. Madan, and J. a van Aalst, "Osteoinduction in umbilical cord- and palate periosteum-derived mesenchymal stem cells.," *Annals of plastic surgery*, vol. 64, no. 5, pp. 605-9, May 2010.

[11] J. P. Dahl, M. Caballero, A. K. Pappa, G. Madan, W. W. Shockley, and J. a van Aalst, "Analysis of human auricular cartilage to guide tissue-engineered nanofiber-based chondrogenesis: implications for microtia reconstruction.," *Otolaryngology—head and neck surgery: official journal of American Academy of Otolaryngology—Head and Neck Surgery*, vol. 145, no. 6, pp. 915-23, Dec. 2011.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A system for engineering a tissue, comprising:
a transmitter configured to transmit a signal to a receiver; and
an implantable bioreactor, comprising:
   a receiver configured to receive a signal from a transmitter;
   a holding structure comprising a cell compartment having an open cavity configured to hold one or more mesenchymal stem cells (MSC) within an interior of the open cavity of the cell compartment; and
   a vibratory actuator in communication with the receiver and configured to generate a vibratory signal;
wherein the holding structure is adjacent to the vibratory actuator within the implantable bioreactor;
wherein a signal transmitted from the transmitter and received by the receiver is communicated to the vibratory actuator to generate a vibratory signal, wherein the vibratory signal is applied to the MSC within the interior of the open cavity of the cell compartment,
wherein the receiver, holding structure and vibratory actuator are configured to be implantable into a subject's body, wherein the transmitter is configured to be external to the subject's body.

2. The system of claim 1, wherein the transmitter comprises any combination of a computer, processor, embedded system, microcontroller and/or computer readable medium, wherein the computer readable medium has stored thereon executable instructions that when executed by the processor of the computer cause the transmitter to transmit a desired signal.

3. The system of claim 1, wherein the signal transmitted by the transmitter and received by the receiver is a wireless signal.

4. The system of claim 1, wherein the transmitter is ex vivo while the receiver is in vivo.

5. The system of claim 1, wherein the vibratory signal generated by the vibratory actuator has a frequency ranging from about 0.1 hertz to about 1000 hertz.

6. The system of claim 5, wherein the vibratory signal generated by the vibratory actuator has a frequency ranging from about 1 hertz to about 100 hertz.

7. The system of claim 1, further comprising a monitoring component for monitoring the differentiation of the MSC subsequent to application of vibratory signals.

8. The system of claim 1, wherein the frequency, duration, amplitude, waveform, and timing of the vibratory signal can be adjusted depending on the differentiation of the MSC.

9. The system of claim 1, wherein the receiver is configured to send a return signal to the transmitter based on the differentiation of the MSC.

10. The system of claim 1, further comprising a bioreactor configured to be implanted in a subject.

11. A system for engineering a tissue, comprising:
a transmitter configured to transmit a signal to a receiver; and
an implantable bioreactor, comprising:
   a receiver configured to receive a signal from a transmitter;
   a holding structure comprising a cell compartment having an open cavity configured to hold one or more mesenchymal stem cells (MSC) within an interior of the open cavity of the cell compartment; MSC within the holding structure; and
   a vibratory actuator in communication with the receiver and configured to generate a vibratory signal;
wherein the holding structure is adjacent to the vibratory actuator within the implantable bioreactor;
wherein a signal transmitted from the transmitter and received by the receiver is communicated to the vibratory actuator to generate a vibratory signal, wherein the vibratory signal is applied to the MSC within the interior of the open cavity of the cell compartment,
wherein the MSC within the holding structure are in sufficient proximity to the vibratory actuator such that the vibratory signal generated by the vibratory actuator is applied to the MSC, to a scaffold onto which MSCs are adherent, and/or to tissue into which MSCs have been delivered.

12. A system for engineering a tissue, comprising:
a transmitter configured to transmit a signal to a receiver; and
an implantable bioreactor, comprising:
   a receiver configured to receive a signal from a transmitter;

a holding structure comprising a cell compartment having an open cavity configured to hold one or more mesenchymal stem cells (MSC) within an interior of the open cavity of the cell compartment;
MSC within the holding structure; and
a vibratory actuator in communication with the receiver and configured to generate a vibratory signal;
wherein the holding structure is adjacent to the vibratory actuator within the implantable bioreactor;
wherein a signal transmitted from the transmitter and received by the receiver is communicated to the vibratory actuator to generate a vibratory signal, wherein the vibratory signal is applied to the MSC within the interior of the open cavity of the cell compartment,
further comprising a monitoring component for non-damaging or non-destructive measurement or quantification of the differentiation of the MSC subsequent to application of vibratory signals.

13. The system of claim 12, wherein the monitoring component uses signals to exert feedback control over the course of tissue differentiation.

14. The system of claim 13, wherein a real-time status of MSC development or phenotype is conveyed to the external monitoring system using wireless signals and the feedback control signals.

15. The system of claim 13, wherein a past time-course of MSC development or phenotype is stored on the implantable device and may thereafter be conveyed to the external monitoring system using wireless signals.

* * * * *